(12) United States Patent
Roichman et al.

(10) Patent No.: US 10,827,915 B2
(45) Date of Patent: Nov. 10, 2020

(54) METHOD AND SYSTEM FOR IMAGING INTERNAL MEDIUM

(71) Applicant: Ramot at Tel-Aviv University Ltd., Tel-Aviv (IL)

(72) Inventors: Yael Roichman, Tel-Aviv (IL); Elad Dekel, Tel-Aviv (IL); Dror Kasimov, Tel-Aviv (IL); Harel Nagar, Tel-Aviv (IL); Tsafrir Kolatt, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/323,543

(22) PCT Filed: Aug. 7, 2017

(86) PCT No.: PCT/IL2017/050871
§ 371 (c)(1),
(2) Date: Feb. 6, 2019

(87) PCT Pub. No.: WO2018/029678
PCT Pub. Date: Feb. 15, 2018

(65) Prior Publication Data
US 2019/0191979 A1    Jun. 27, 2019

Related U.S. Application Data

(60) Provisional application No. 62/371,781, filed on Aug. 7, 2016, provisional application No. 62/444,436, filed on Jan. 10, 2017.

(51) Int. Cl.
*G02B 21/10* (2006.01)
*A61B 1/06* (2006.01)
(Continued)

(52) U.S. Cl.
CPC .......... *A61B 1/0653* (2013.01); *A61B 1/0005* (2013.01); *A61B 1/00009* (2013.01);
(Continued)

(58) Field of Classification Search
CPC .. G02B 6/0076; G02B 21/0044; G02B 21/06; G02B 21/10; G02B 21/32; G02B 26/106;
(Continued)

(56) References Cited

U.S. PATENT DOCUMENTS 5,416,582 A    5/1995  Knutson et al.
5,583,342 A   12/1996  Ichie
(Continued)

FOREIGN PATENT DOCUMENTS

EP       2977810        1/2016
JP       2002-102146    4/2002
WO       WO 2018/029678 2/2018

OTHER PUBLICATIONS

International Preliminary Report on Patentability dated Feb. 21, 2019 From the International Bureau of WIPO Re. Application No. PCT/IL2017/050871. (9 Pages).
(Continued)

*Primary Examiner* — David P Porta
*Assistant Examiner* — Fani Boosalis

(57) ABSTRACT

A method of imaging through a medium is disclosed. The method comprises: illuminating the medium by a non-diffracting light beam over a plurality of locations on a boundary of the medium; collecting back scattered light for each location of the light beam; and constructing an image based on intensity levels of the back scattered light at each of the plurality of locations, the intensity levels constituting local contrasts over the image.

22 Claims, 11 Drawing Sheets
(9 of 11 Drawing Sheet(s) Filed in Color)

(51) Int. Cl.
| | |
|---|---|
| G02B 26/10 | (2006.01) |
| G02B 21/00 | (2006.01) |
| G02B 21/32 | (2006.01) |
| G02B 6/42 | (2006.01) |
| G02B 21/06 | (2006.01) |
| A61B 1/00 | (2006.01) |
| A61B 1/07 | (2006.01) |

(52) U.S. Cl.
CPC .............. *A61B 1/063* (2013.01); *A61B 1/07* (2013.01); *G02B 6/4292* (2013.01); *G02B 21/0076* (2013.01); *G02B 21/06* (2013.01); *G02B 21/10* (2013.01); *G02B 21/32* (2013.01); *G02B 26/106* (2013.01); *G02B 21/0044* (2013.01)

(58) Field of Classification Search
CPC .... G02B 6/4292; G02B 6/00; A61B 1/00009; A61B 1/063; A61B 1/0653; A61B 1/07
See application file for complete search history.

(56) References Cited

U.S. PATENT DOCUMENTS

| | | | |
|---|---|---|---|
| 6,982,790 | B1 | 1/2006 | Gershenson |
| 8,554,087 | B2 | 10/2013 | Osterberg |
| 9,220,412 | B2 | 12/2015 | Cuccia |
| 2005/0187478 | A1 | 8/2005 | Beaudry et al. |
| 2011/0205352 | A1 | 8/2011 | Pavani et al. |
| 2012/0081518 | A1 | 4/2012 | Liu et al. |
| 2014/0285653 | A1 | 9/2014 | Betzig |
| 2017/0160531 | A1 | 6/2017 | Knebel |
| 2019/0041634 | A1* | 2/2019 | Popovich ............. G02B 27/017 |

OTHER PUBLICATIONS

International Search Report and the Written Opinion dated Dec. 7, 2017 From the International Searching Authority Re. Application No. PCT/IL2017/050871. (15 Pages).

Agarwal et al. "Manipulation and Assembly of Nanowires With Holographic Optical Traps", Optics Express, 13(22): 8906-8912, Oct. 31, 2005.

Broky et al. "Self-Healing Properties of Optical Airy Beams", Optics Express, 16(17): 12880-12891, Aug. 18, 2008.

Calafiore et al. "Nanoimprint of a 3D Structure on an Optical Fiber for Light Wavefront Manipulation", Nanotechnology, 27(37): 375301-1-375301-7, Aug. 8, 2016.

Curatolo et al. "Quantifying the Influence of Bessel Beams on Image Quality in Optical Coherence Tomography", Scientific Reports, 6(23483): 1-12, Mar. 24, 2016.

Dunsby et al. "Techniques for Depth-Resolved Imaging Through Turbid Media Including Coherence-Gated Imaging", Journal of Physics D: Applied Physics, 36(14): R207-R227, Jul. 1, 2003.

Fahrbach et al. "Microscopy With Self-Reconstructing Beams", Nature Photonics, 4(11): 780-785, Published Online Sep. 12, 2010.

Fahrbach et al. "Propagation Stability of Self-Reconstructing Bessel Beams Enables Contrast-Enhanced Imaging in the Thick Media", Nature Communications, 3(632): 1-8, Jan. 17, 2012.

Habaza et al. "Tomographic Phase Microscopy With 180° Rotation of Live Cells in Suspension by Holographic Optical Tweezers", Optics Letters, 40(8): 1881-1884, Apr. 15, 2015.

Jia et al. "Isotropic 3D Super-Resolution Imaging With a Self-Bending Point Spread Function", Nature Photonics, 8(4): 302-306, Published Online Mar. 2, 2014.

Malinauskas et al. "Femtosecond Laser Fabrication of Hybrid Micro-Optical Elements and Their Integration on the Fiber Tip", Proceedings of the SPIE, Micro-Optics 2010, 7716: 77160A-1-77160A-12, Apr. 30, 2010.

Ntziachristos "Going Deeper Than Microscopy: The Optical Imaging Frontier in Biology", Nature Methods, 7(8): 603-614, Published Online Jul. 30, 2010.

Vettenburg et al. "Light Sheet Microscopy Using an Airy Beam", Nature Methods, 11(5): 541-544, Published Online Apr. 6, 2014.

Yevnin et al. "Independent and Simultaneous Three-Dimensional Optical Trapping and Imaging", Biomedial Optics Express, 4(10): 2087-2094, Published Online Sep. 9, 2013.

Supplementary European Search Report and the European Search Opinion dated Feb. 17, 2020 From the European Patent Office Re. Application No. 17838923.5. (10 Pages).

* cited by examiner

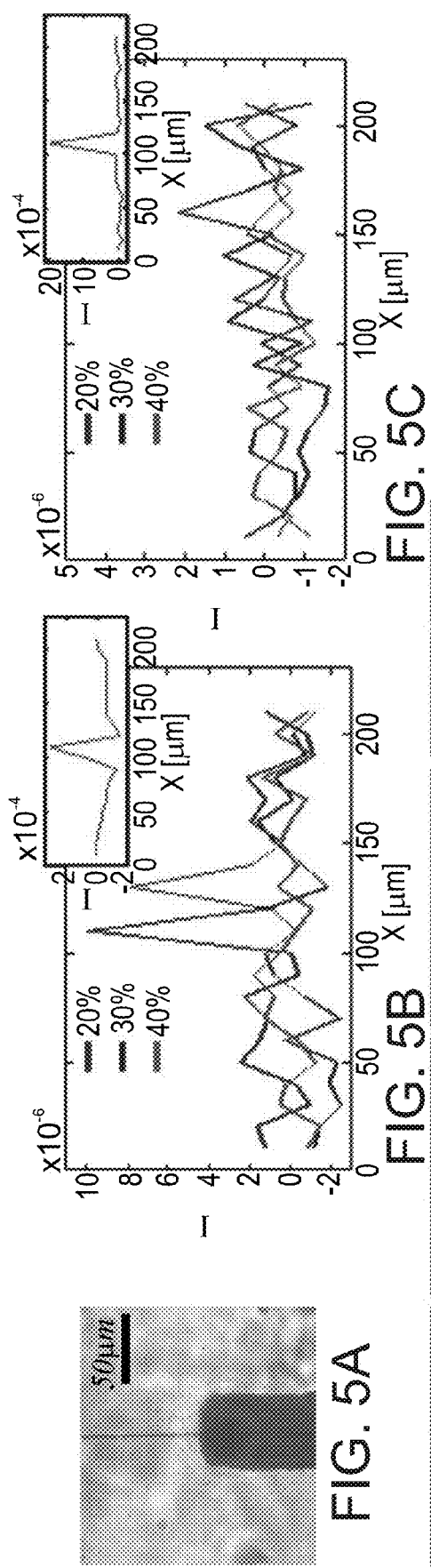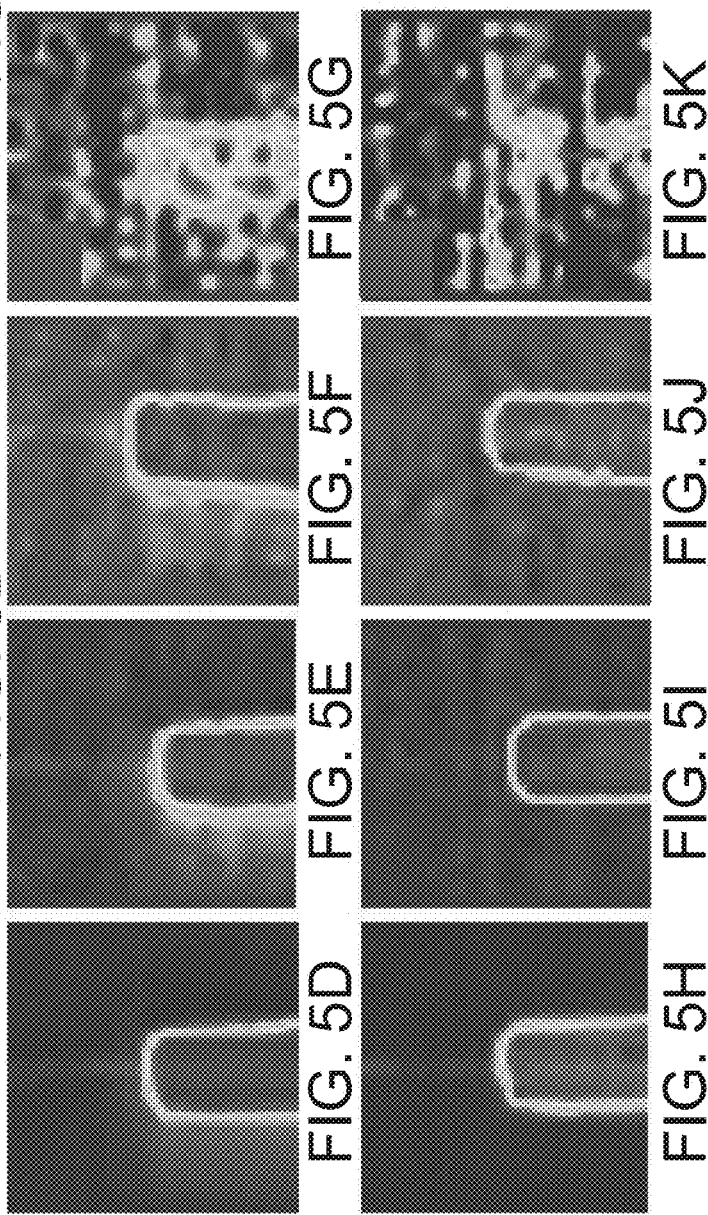

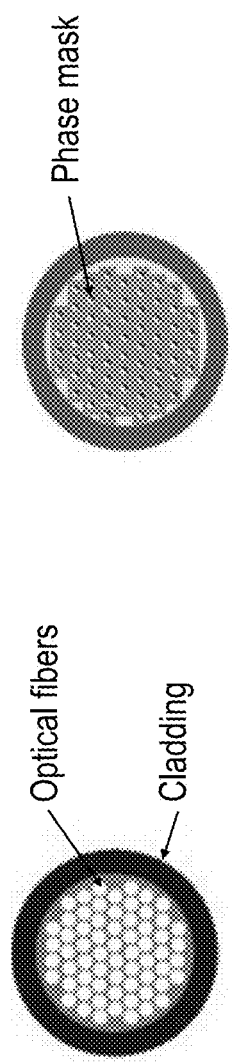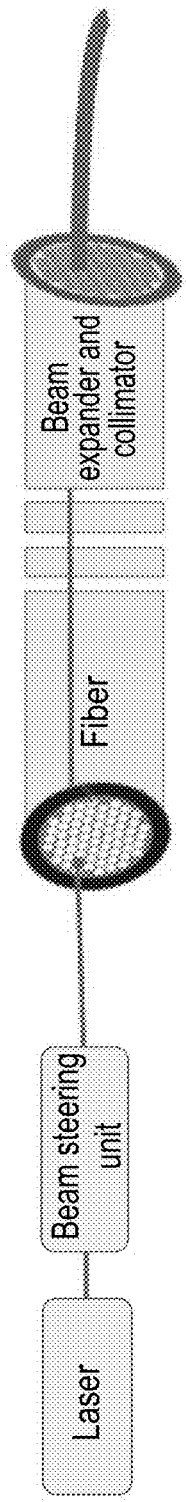

METHOD AND SYSTEM FOR IMAGING INTERNAL MEDIUM

RELATED APPLICATIONS

This application is a National Phase of PCT Patent Application No. PCT/IL2017/050871 having International filing date of Aug. 7, 2017, which claims the benefit of priority under 35 USC § 119(e) of U.S. Provisional Patent Application Nos. 62/371,781 filed on Aug. 7, 2016 and 62/444,436 filed on Jan. 10, 2017. The contents of the above applications are all incorporated by reference as if fully set forth herein in their entirety.

FIELD AND BACKGROUND OF THE INVENTION

The present invention, in some embodiments thereof, relates to imaging and, more particularly, but not exclusively, to a method and system for imaging internal medium.

There are numerous imaging techniques to produce an image of an internal medium, e.g., a biological medium. These techniques employ, inter alia, X-rays, magnetic resonance imaging (MRI), positron emission tomography (PET) scans and ultrasound.

It is oftentimes desired, however, to employ optical imaging. Some techniques for imaging through turbid media have been developed to overcome the challenge of scattering of the imaging light by biological organelles. These techniques are based on wave front shaping, time gated imaging, interferometric detection, and multiphoton microscopy [see, e.g., Ntziachristos, Nature methods 7, 603-14 (2010); and Dunsby and French, Journal of Physics D: Applied Physics 36, 14: R207-R227 (2003)].

Additional background art includes Agarwal et al., Optics Express. 2005 Oct. 31; 13(22):8906-12; Habaza et al., Optics letters. 2015 Apr. 15; 40(8):1881-4; Yevnin et al., Biomedical optics express. 2013 Oct. 1; 4(10):2087-94; Malinauskas et al., SPIE Photonics Europe 2010 Apr. 30 (pp. 77160A-77160A), International Society for Optics and Photonics; Calafiore et al., Nanotechnology 27, 375301 (2016); U.S. Pat. Nos. 6,982,790 and 8,554,087, and U.S. Published Application No. 20050187478.

SUMMARY OF THE INVENTION

According to some embodiments of the invention the present invention there is provided a method of imaging through a medium. The method comprises: illuminating the medium by a non-diffracting light beam over a plurality of locations on a boundary of the medium; collecting back scattered light for each location of the light beam; and constructing an image based on intensity levels of the back scattered light at each of the plurality of locations, the intensity levels constituting local contrasts over the image.

According to an aspect of some embodiments of the present invention there is provided a method of imaging through a medium that has fluorescent molecules. The method comprises: illuminating the medium by a non-diffracting light beam over a plurality of locations on a boundary of the medium to excite the fluorescent molecules; for each location of the light beam, collecting light emitted by the fluorescent molecules responsively to the excitation; and constructing an image based on intensity levels of the emitted light at each of the plurality of locations, the intensity levels constituting local contrasts over the image.

According to some embodiments of the invention the method comprises illuminating the medium by at least one additional non-diffracting light beam, different from the non-diffracting light beam, and calculating a depth of the medium or an object in the medium based on a comparison between intensity levels received for different beams.

According to some embodiments of the invention the illumination comprises scanning the medium the light beam.

According to some embodiments of the invention the scanning is by a holographic optical tweezers system.

According to some embodiments of the invention the illumination comprises projecting a structured light beam onto the medium.

According to some embodiments of the invention the illumination comprises sequentially illuminating the medium by a plurality of non-diffracting light beams, wherein each non-diffracting light beam is characterized by a different central wavelength.

According to some embodiments of the invention the illumination comprises guiding a first light beam through a waveguide system having a proximal end and a distal end, and transforming the first light beam into the non-diffracting light beam at the distal end.

According to some embodiments of the invention the illumination comprises scanning the medium by the non-diffracting light beam.

According to some embodiments of the invention the waveguide system comprises an optical fiber bundle, wherein the scanning comprises scanning the proximal end by the first light beam.

According to some embodiments of the invention the medium is an internal cavity of a living body.

According to some embodiments of the invention the internal cavity is a blood vessel.

According to some embodiments of the invention the internal cavity is a urethra.

According to some embodiments of the invention the internal cavity is a gastrointestinal tract.

According to some embodiments of the invention the internal cavity is a fallopian tube.

According to some embodiments of the invention the internal cavity is a pancreas.

According to some embodiments of the invention the internal cavity is a bladder.

According to some embodiments of the invention the internal cavity is selected from the group consisting of an esophagus, a trachea, a bronchus, a larynx, a sinus and an ear canal.

According to some embodiments of the invention illumination comprises sequentially illuminating the medium by a plurality of non-diffracting light beams, wherein each non-diffracting light beam is characterized by a different central wavelength.

According to some embodiments of the invention the sequentially illumination comprises sequentially filtering a polychromatic light beam, such that at each filtering the first light beam is characterized by a different central wavelength.

According to some embodiments of the invention at each filtering, the first light beam is diverted along a different optical path prior to entering the proximal end.

According to some embodiments of the invention at each filtering, the first light beam is diverted along the same optical path prior to entering the proximal end.

According to an aspect of some embodiments of the present invention there is provided a system for imaging through a medium, the system comprising: an illumination system configured for illuminating the medium by a nondiffracting light beam over a plurality of locations on a boundary of the medium; a light detecting system configured for collecting light for each location of the light beam; and an image processor configured for processing intensity levels of the light at each of the plurality of locations, and constructing an image based on the intensity levels, the intensity levels constituting local contrasts over the image.

According to some embodiments of the invention the illumination system comprises a scanning system for scanning the medium with the light beam.

According to some embodiments of the invention the scanning is by holography.

According to some embodiments of the invention the scanning system comprises a holographic optical tweezers system.

According to some embodiments of the invention the illumination system comprises a structured light projector.

According to some embodiments of the invention the illuminating system is configured to sequentially illuminate the medium by a plurality of non-diffracting light beams, wherein each non-diffracting light beam is characterized by a different central wavelength.

According to some embodiments of the invention the illumination system comprises a light source configured for producing a first light beam, a waveguide system having a proximal end for receiving first light beam and a distal end for emitting the first light beam, and a beam transforming element at the distal end for transforming the first light beam into the non-diffracting light beam.

According to some embodiments of the invention the waveguide system comprises an optical fiber.

According to some embodiments of the invention the waveguide system comprises an optical fiber bundle.

According to some embodiments of the invention the waveguide system comprises a beam expander at the distal end.

According to some embodiments of the invention the waveguide system comprises a collimator at the distal end.

According to some embodiments of the invention the system comprises a scanning system configured for scanning the medium by the non-diffracting light beam.

According to some embodiments of the invention the waveguide system comprises an optical fiber bundle and wherein the scanning system is configured for scanning the proximal end by the first light beam.

According to some embodiments of the invention the light source is configured for providing a polychromatic light beam, wherein the system comprises a sequential filter configured for sequentially filtering the polychromatic light beam such that at each filtering the first light beam is characterized by a different central wavelength.

According to some embodiments of the invention the system comprises an arrangement of beam diverting elements configured to divert different central wavelengths of the first light beam along a different optical path prior to entering the proximal end.

According to some embodiments of the invention the non-diffracting light beam is a Bessel beam.

According to some embodiments of the invention the non-diffracting light beam is an Airy beam.

According to some embodiments of the invention the non-diffracting light beam is a super Airy beam.

According to some embodiments of the invention the non-diffracting light beam is a Mathieu beam.

According to some embodiments of the invention the non-diffracting light beam is a Weber beam.

According to some embodiments of the invention the non-diffracting light beam is a one-dimensional beam.

According to some embodiments of the invention the non-diffracting light beam is a two-dimensional beam.

According to some embodiments of the invention a coefficient or a parameter of the non-diffracting light beam is selected to allow the non-diffracting light beam to penetrate at least 100 μm into the medium.

According to some embodiments of the invention the non-diffracting light beam is at an infrared wavelength.

According to some embodiments of the invention the non-diffracting light beam is at a near-infrared wavelength.

According to some embodiments of the invention the non-diffracting light beam is at a visible wavelength.

According to some embodiments of the invention the image is a three-dimensional image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of an experimental system used in experiments performed according to some embodiments of the present invention;

FIGS. 2A and 2B show phase masks of one-dimensional (FIG. 2A) and two-dimensional (FIG. 2B) Airy beams, generated and used in experiments performed according to some embodiments of the present invention;

FIGS. 2C and 2D show reflections of the Airy beams shown in FIGS. 2A and 2B, respectively, as measured in experiments performed according to some embodiments of the present invention;

FIGS. 2E and 2F show reflections of the Airy beams shown in FIGS. 2A and 2B, respectively, as obtained by computer simulations performed according to some embodiments of the present invention;

FIG. 3 shows microscope images of Airy beams reflected from a mirror with different values of a scaling parameter, as obtained in experiments performed according to some embodiments of the present invention;

FIGS. 4A and 4B show measured and calculated three-dimensional structures of a light beam in water, as obtained in experiments performed according to some embodiments of the present invention;

FIGS. 4C and 4D show intensity distribution and shape of beams in double distilled water (FIG. 4C) and milk (FIG. 4D), as obtained in experiments performed according to some embodiments of the present invention;

Figure 1:
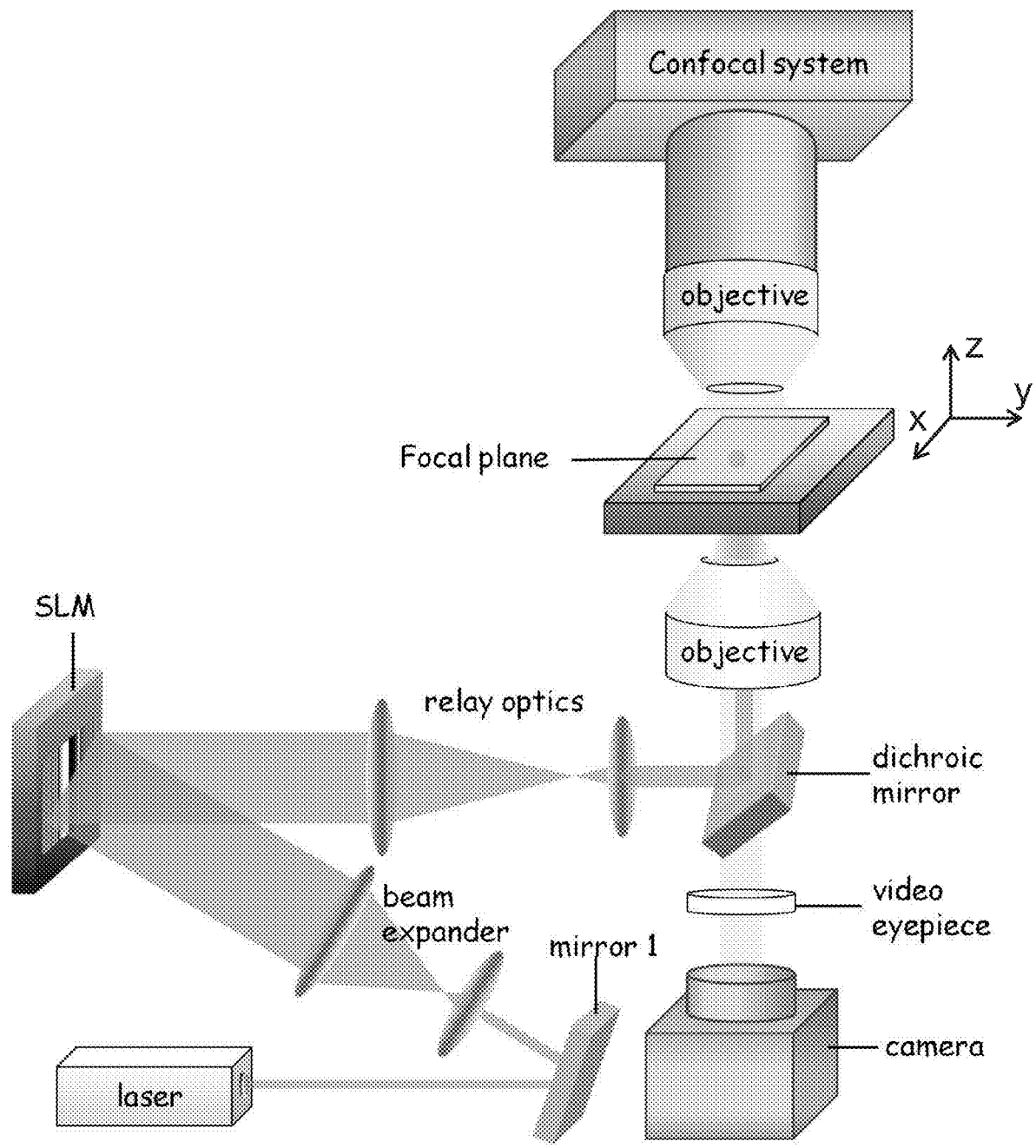
Figure 6:
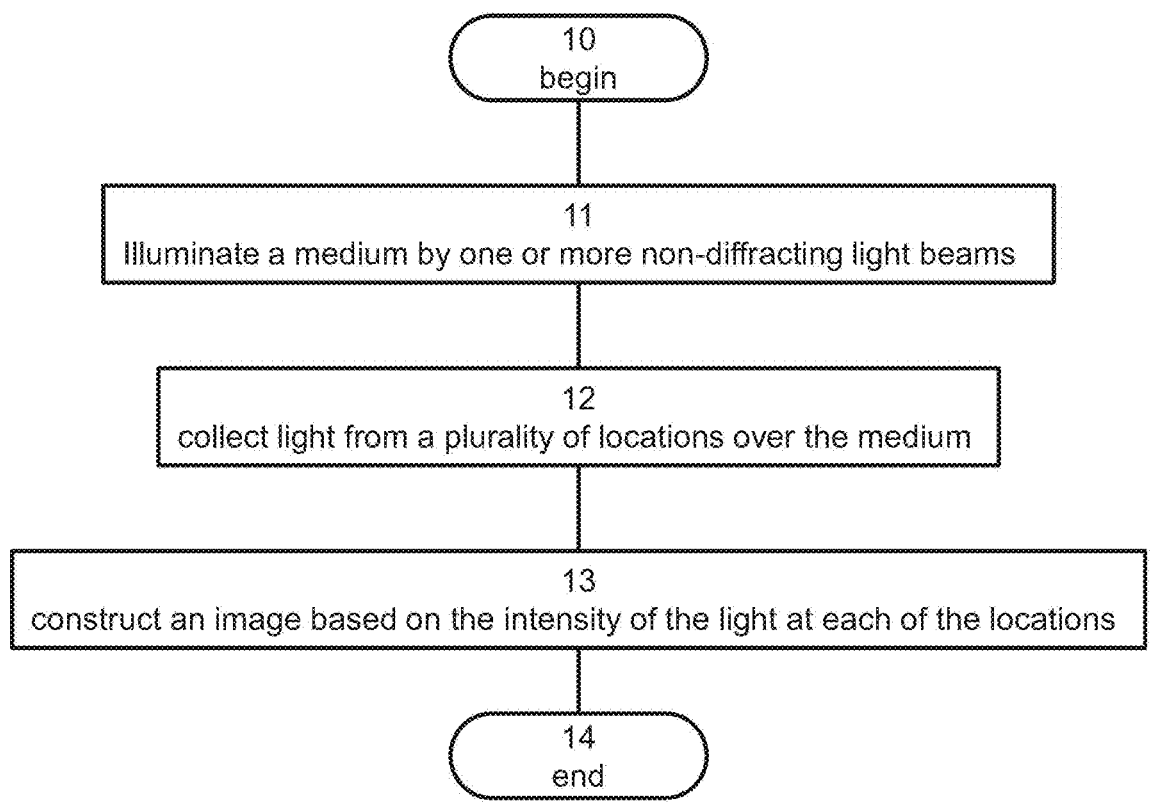
Figure 7A:
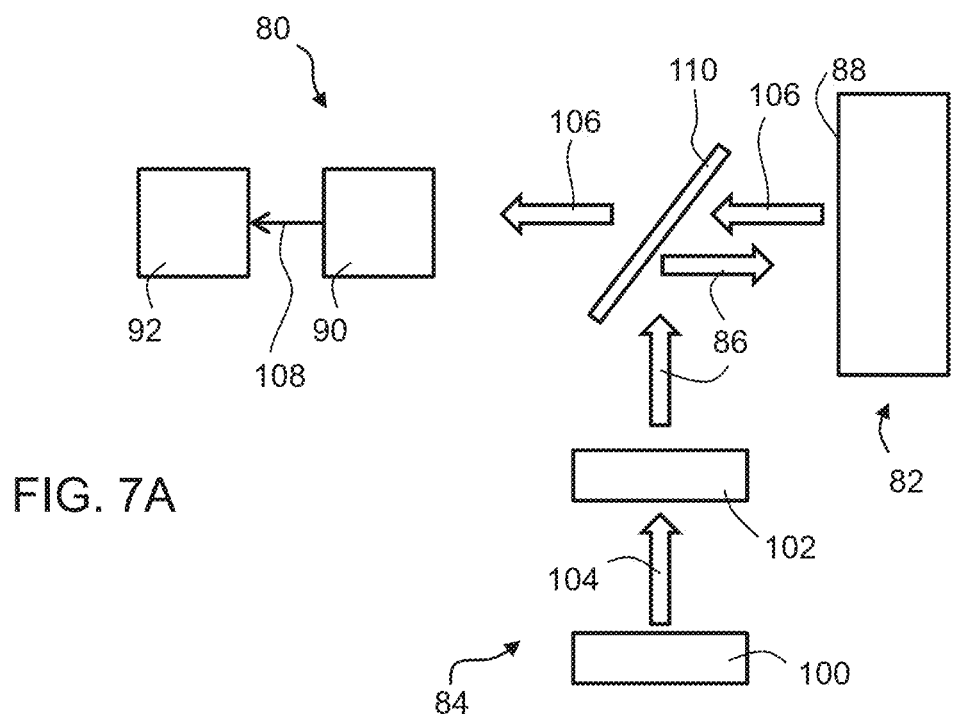
Figure 7B:
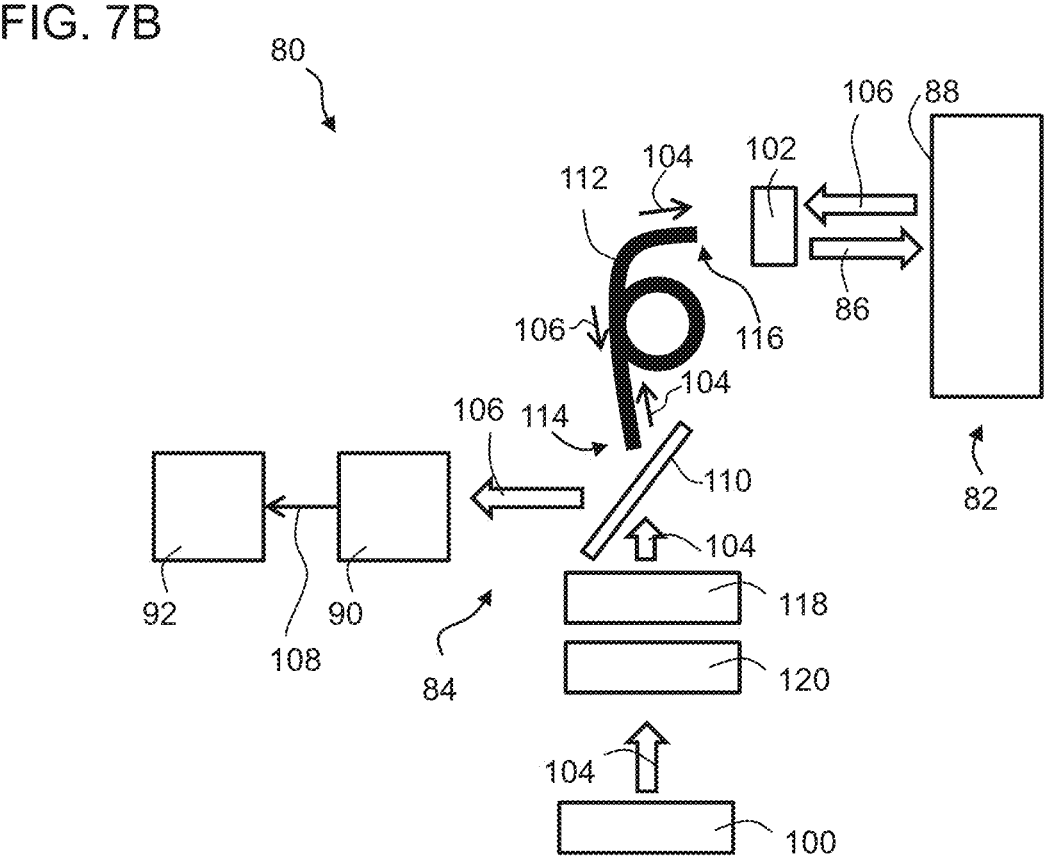
Figure 8:
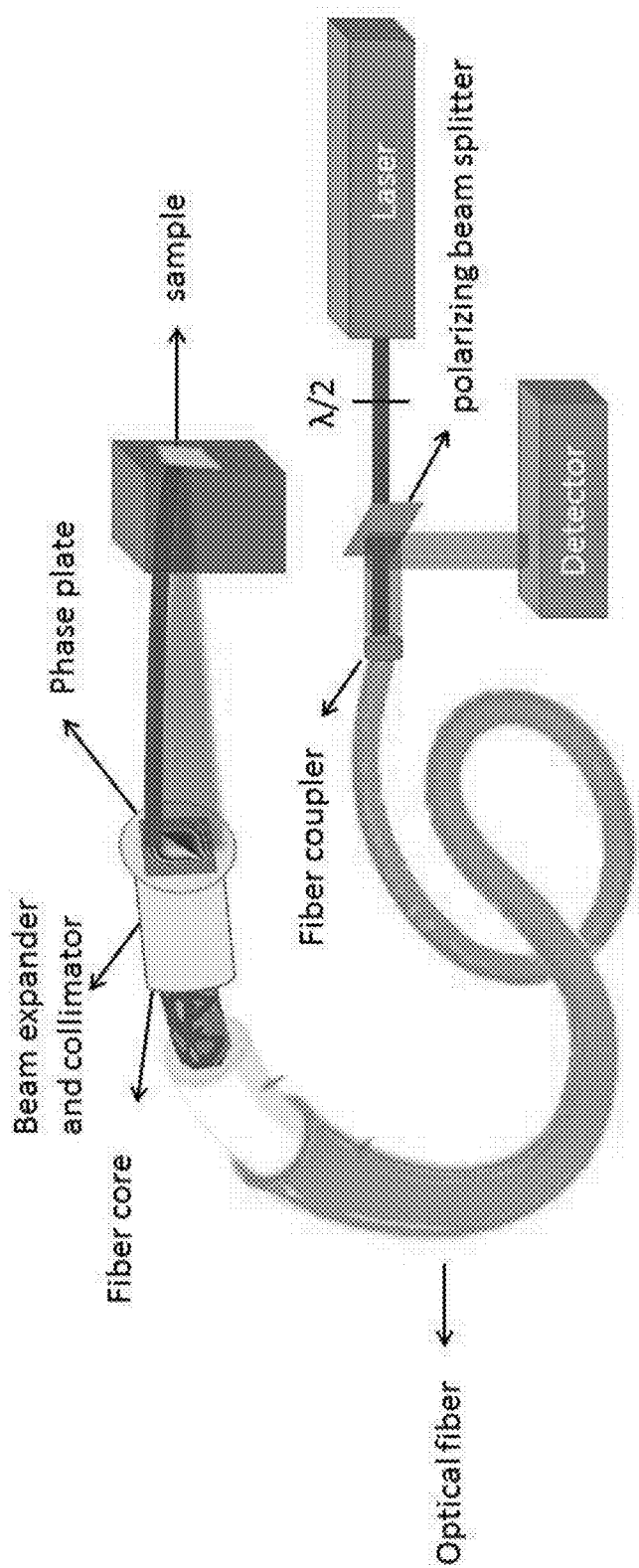
Figure 9:
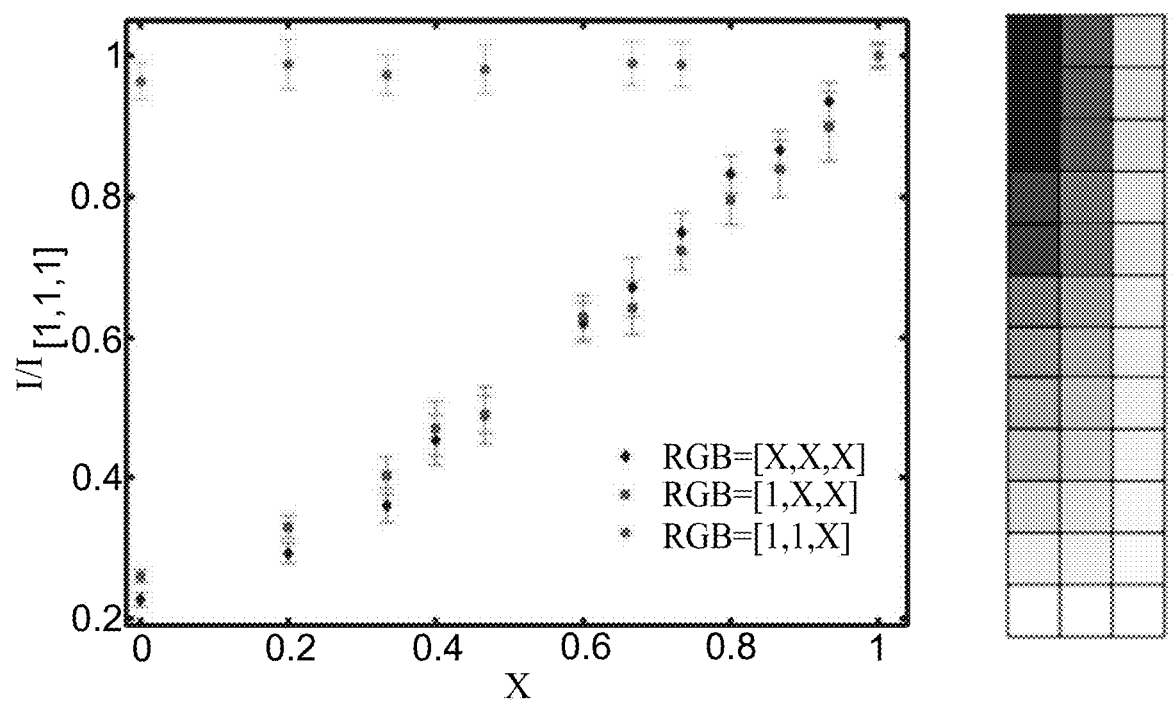
Figure 10A:
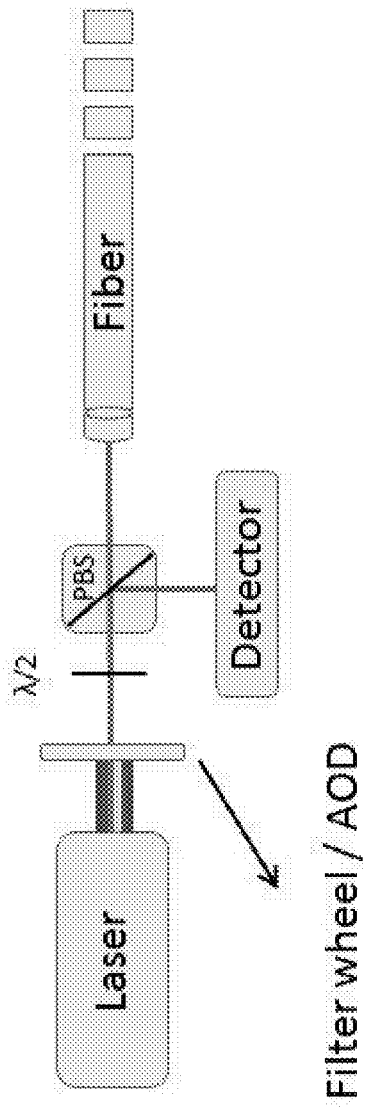
Figure 10B:
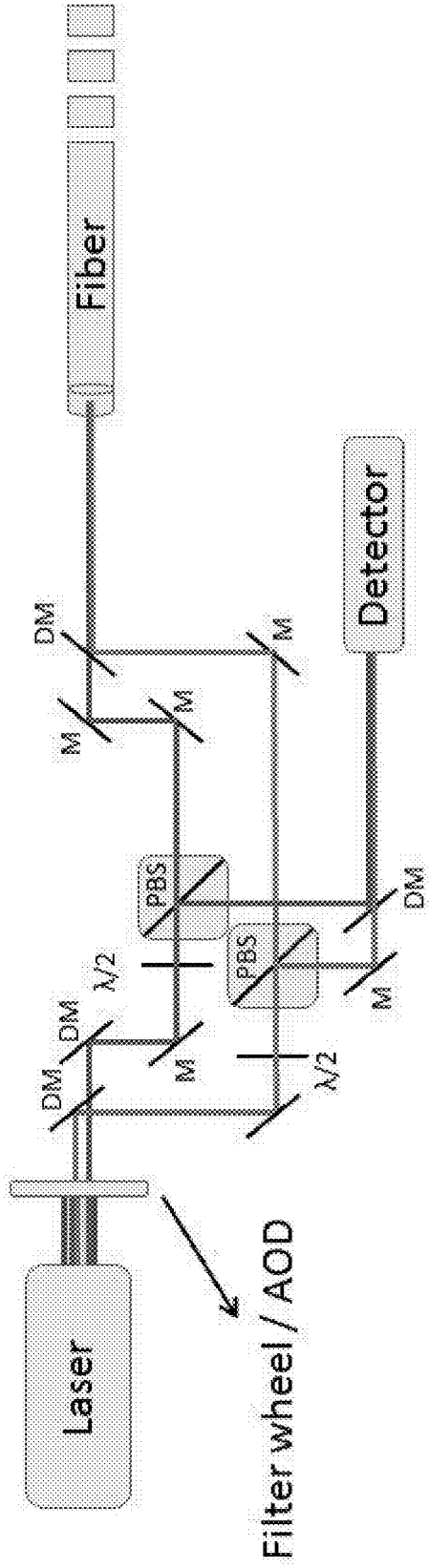

FIGS. 5A-K show results of experiments of imaging through turbid medium, performed according to some embodiments of the present invention FIG. 6 is a flowchart diagram of a method suitable for imaging a medium according to various exemplary embodiments of the present invention;

FIGS. 7A and 7B are schematic illustrations of a system for imaging through a medium, according to some embodiments of the present invention;

FIG. 8 is a schematic illustration of a system for imaging through a medium, according to embodiments of the present invention in which a non-diffracting light beam is formed at the exit of a waveguide system;

FIG. 9 shows relative intensity reflected from a target as measured using the experimental system shown in FIG. 1, using a laser working at a wavelength of 532 nm;

FIGS. 10A and 10B are schematic illustrations showing techniques suitable for coupling a polychromatic light beam into a waveguide system according to some embodiments of the present invention; and FIGS. 11A-C are schematic illustrations showing a waveguide system suitable for beam scanning, according to some embodiments of the present invention.

DETAILED DESCRIPTION OF SPECIFIC EMBODIMENTS OF THE INVENTION

The present invention, in some embodiments thereof, relates to imaging and, more particularly, but not exclusively, to a method and system for imaging internal medium.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The method and system of the present embodiments are particularly useful for imaging an interior of an optically turbid medium, or for imaging a clear medium through an optically turbid medium.

A turbid medium is a substance consisting of a material having a high light-scattering coefficient. Representative examples of turbid media that can be imaged by the method and system of the present embodiments include, without limitation, a biological tissue, a biological fluid, an intralipid solution, ice, fog, snow and seawater.

The interior of the turbid medium to be imaged typically has at least two components, a base component having a first set of optical properties, and a scattering component having a second set of optical properties. When photons pass through the turbid medium, they may pass through the base medium component between the scattering particles, and not be affected by the scattering component. These photons are referred to as ballistic photons. Other photons may pass through the base component until they scattered off particles forming the scattering component. These photons may then be deflected or reflected through a distribution of deflection angles by their interaction with the particles. The distribution of deflection angles vary with the wavelength of the photons, the size of the particles, and the optical properties of the base component and the scattering component. Photons may undergo multiple interactions with scattering particles, as well as an object of interest.

Some turbid media, such as a biological tissue or a biological fluid, are considerably more complex, and may include a wide range of scattering particles and, at times it may be difficult to distinguish between the base medium and the scattering particles. Photons penetrating such media can be divided into populations of ballistic photons, snake photons, and diffusive photons. Typically, the diffusive population becomes large relative to the ballistic population, resulting in an impaired vision through the media.

The present embodiments successfully overcome the difficulty in viewing the interior of a turbid medium and can be used in a variety of applications. For example, the method and system of the present embodiments can be used for imaging foreign objects through human or animal blood and/or tissue. The method and system of the present embodiments can also be used for imaging of an internal cavity, e.g., an internal cavity of a human or animal subject, through a waveguide system, such as, but not limited to, an optical fiber and optical fiber bundle, guided through the internal cavity or through a channel into the internal cavity. For example, method and system of the present embodiments can be used in medical imaging, such as, but not limited to, angioscopy through a waveguide system guided through a blood vessel, imaging of kidney stones through a waveguide system guided through the urethra, imaging of cerebrospinal fluid (CSF) through a waveguide system guided through the spinal entry, and imaging during minimally invasive procedures, e.g., heart catheterization and other cardiovascular procedures. The method and system of the present embodiments can also be used for imaging a vehicle through fog or clouds. The method and system of the present embodiments can also be used for imaging through filled or fiber-reinforced articles (e.g., plastics). The method and system of the present embodiments can also be used for imaging the interior of murky water, e.g., for the purpose of searching for objects therein.

Referring now to the drawings, FIG. 6 is a flowchart diagram of a method suitable for imaging a medium according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

Some operations of the method are optionally and preferably executed using an image processor, more preferably a digital image processor, which can be embodied as dedicated circuitry or a general purpose computer configured for executing the respective operations. For example, selected operations of the method can be embodied on the dedicated circuitry as computer instructions for performing the operations. Selected operations can be embodied on a computer readable medium, comprising computer readable instructions for carrying out the operations. Computer programs implementing these operations can commonly be distributed to users on a distribution medium such as, but not limited to, a floppy disk or CD-ROM or flash memory media. From the distribution medium, the computer programs can be copied to a hard disk or a similar intermediate storage medium. In some embodiments of the present invention, computer programs implementing selected operations of the method of the present embodiments can be distributed to users by allowing the user to download the programs from a remote location, via a communication network, e.g., the internet. The computer programs can be run by loading the computer instructions either from their distribution medium or their intermediate storage medium into the execution memory of the computer, configuring the computer to act in accordance with the respective operations. All these operations are well-known to those skilled in the art of computer systems.

The computational operations of the method of the present embodiments can be executed either remote from the medium or near the medium. When the computer is remote from the medium, it can receive the data over a network, such as a telephone network or the Internet. To this end, a local computer can be used to transmit the data to the remote computer. This configuration allows generating the image while the medium is at a different location, and also allows performing simultaneous analyses for multiple media in multiple different locations.

The computational operations of the method can also be executed by a cloud computing resource of a cloud computing facility. The cloud computing resource can include a computing server and optionally also a storage server, and can be operated by a cloud computing client as known in the art.

The method begins at 10 and optionally and preferably continues to 11 at which the medium is illuminated by a non-diffracting light beam over a plurality of location on a boundary of the medium.

As used herein, a "non-diffracting beam," refers to a field of electromagnetic radiation that experiences no diffraction over a propagation distance of at least three times longer than the depth of focus of the beam, or experiences diffraction resulting in a rate of change of less than 10% per focal depth in the beam's waist.

Representative examples for a non-diffracting beam according to some embodiments of the present invention including, without limitation, an Airy beam, a super Airy beam, a Bessel beam, a Weber beam, and a Mathieu beam.

A non-diffracting beam can optionally and preferably be generated by transmitting a diffracting beam (e.g., a Gaussian beam) through a phase mask (such as, but not limited to, a Spatial Light Modulator device), having a spatial phase pattern selected to accord the beam with a phase profile in accordance with the type of the non-diffracting beam.

One or more of the characteristics of the beam is optionally and preferably selected to allow the beam to penetrate the medium, and allow constructing an image of the interior of the medium, or of one or more objects within the medium, at a predetermined depth and a predetermined spatial resolution. Thus, for example, the length scale over which the beam maintains its original shape is optionally and preferably selected to be at least the desired, and predetermined, depth (e.g., at least 100 μm or at least 200 μm or at least 300 μm or at least 400 μm or at least 500 μm), and the waist of the beam is optionally and preferably selected to be at most the desired, and predetermined, smallest resolvable lateral dimension (e.g., less than 50 μm or less than 20 μm or less than 10 μm or less than 5 μm). It is recognized that a non-diffracting light beam also exhibit self-acceleration in the form of bending of the light path. The acceleration rate of the beam reduces the penetration depth, but increases the beam's average intensity. Therefore, according to some embodiments of the present invention the acceleration rate of the beam is selected in accordance with the desired depth and the desired sensitivity.

When the beam is an Airy beam, the phase profile can include a cubic term which is proportional to the third power of one or two coordinates along a transverse plane. This can be represented mathematically as $\phi = \vec{x}^3 2\pi \ell$, where $\phi$ is the phase and $\vec{x}$ is a normalized transverse vector coordinate, and $\ell$ is a dimensionless coefficient which can be used as a scaling parameter. The generation of an Airy beam can be carried out using a phase mask having a cubic phase pattern. In case of an Airy beam, a predetermined length scale over which the beam maintains its original shape can therefore be set by a judicial selection of the coefficient of the cubic term (e.g., modulo $2\pi$). In embodiments in which the non-diffracting light beam is generated using a phase mask, converting a diffracting light beam into the non-diffracting light beam, the scaling parameter can be controlled by selecting the phase pattern of the phase mask.

When the beam is a Bessel beam, the beam's profile includes one or more rings of light intensity. Mathematically, a Bessel beam can be approximated by the equation:

$$E(r,\phi,z) = A_o \exp(ik_z Z) J_n(k,r) \exp(\pm in\phi)$$

where E is the amplitude of the beam, r is the radial transverse coordinate, z is the longitudinal coordinate, $\phi$ is the azimuthal transverse coordinate, $J_n$ is the Bessel function of order n, $k_z$ is the wave vector in the z direction, and $A_0$ is a coefficient. The generation of a Bessel beam can be carried out in a number of ways. For example, since a Bessel beam can be represented as a Fourier transform of a ring, an annular slit can be is placed in the back focal plane of a lens and a diffracting light beam (e.g., a Gaussian light beam) can be transmitted through the lens. This generates a cone characterized by an opening angle which can be approximated by $\tan \theta = d/2f$, where d is the diameter of the annular slit and f is the focal length of the lens. In case of an Bessel beam, a predetermined length scale over which the beam maintains its original shape can therefore be set by a judicial selection of the radius R of the annular slit (representing the radius of the ring in the Fourier plane). Thus, in this case, R can be used as a scaling parameter. For example, when it is desired to obtain a penetration depth of $z_{max}$, the radius of the annular slit can be selected to approximately satisfy the relation $z_{max} = R/\tan \theta$.

When the beam is a Weber beam, the beam propagates along a parabolic line, and the curvature of the parabola can be used as a scaling parameter. Mathematically, the phase profile a Weber beam can be approximated as:

$$\Psi(f_x) = (k^2 - f_x^2)^{-0.5} \exp\left(i\beta\left(\frac{f_x}{k} - \arcsin\left(\frac{f_x}{k}\right)\right)\right),$$

where $f_x$ represents a transverse spatial frequency, and $\beta$ is a parameter that can be used a scaling parameter, which can be set by the size of the aperture of the lens through which the beam is transmitted.

When the beam is a Mathieu beam, the beam propagates along an elliptical line, which can be conveniently described by elliptical transverse radial coordinate $\xi$ and elliptical transverse angular coordinate $\eta$, which can be defined using the Cartesian transverse coordinates x and y, by the relation x=h cos h$\xi$ cos $\eta$ and y=h sin h$\xi$ sin $\eta$, where h is half the distance between the foci of the ellipse. A Mathieu beam can be generated, for example, by generating, for example, using a spatial light modulator, a ring-shaped light field with an azimuthal field dependence. In case of a Mathieu beam, there are optionally and preferably two scaling parameters that define elliptical line (for example, the lengths of the two semiaxes of the ellipse, or the length of one semiaxis and h). Alternatively, the ellipticity of the path of propagation can be used as a scaling parameter. The scaling parameters can be set by the size of the aperture of the lens through which the beam is transmitted and the radius of the ring of the light field.

The light beam can be a one-dimensional beam, in which the phase of the optical field varies along one lateral direction (perpendicular to the propagation direction of the beam) and remains constant along the other lateral direction. Alternatively, the light beam can be a two-dimensional beam, in which the phase of the optical field varies along both lateral directions. The advantage of using a one-dimensional beam is that it provides less stray light in the sample, and the advantage of using a two-dimensional beam is that it provides narrower waist of the probing beam in both x and y directions.

The operation 11 can include two-dimensional scanning of a focal point of the beam over the boundary of the medium. Alternatively, the operation 11 can include structured light projection. Scanning is preferred from the standpoint of spatial resolution and accuracy, and structured light projection is preferred from the standpoint of speed.

When scanning is employed, it can be achieved by any scanning technique known in the art, including, without limitation, holography (e.g., using a holographic optical tweezers system), mechanical scanning (e.g., using a MEMS, or other rotating optical redirector), and the like. When the medium is illuminated by a structured light beam, a structured light projector is typically employed. The structured light projector can include one or more light sources and one or more spatial light modulators, as Optionally, the medium includes fluorescent molecules. In these embodiments, the light beam can be monochromatic with a wavelength selected within the excitation band of the fluorescent molecules. When fluorescent molecules of different excitation bands are used, the light beam can be polychromatic with at least one wavelength for each excitation band. Alternatively, a monochromatic light beam can be used and the wavelength of the beam can be varied to sequentially match the excitation bands of the fluorescent molecules.

In some embodiments of the present invention a light beam is transmitted through a waveguide system (e.g., an optical fiber or an optical fiber bundle) having a proximal end and a distal end, and is transformed into a non-diffracting light beam at the distal end. A representative example of these embodiments is described in the Examples section that follows (see Example 2). The waveguide system can comprise a beam expander and/or a collimator at the distal end. When the light beam is transmitted through waveguide system, the illumination 11 preferably includes scanning the medium by the light beam, after it has been transformed into non-diffracting light beam. When the waveguide system is an optical fiber bundle, the scan optionally and preferably comprises scanning the proximal end by the transmitted light beam.

Embodiments in which a light beam is transmitted through a waveguide system and is transformed into a non-diffracting light beam at the distal end of the waveguide system are particularly useful when the medium is an internal cavity of a living body, such as, but not limited to, a blood vessel, a urethra, a gastrointestinal tract, a fallopian tube, a pancreas, a bladder, an esophagus, a trachea, a bronchus, a larynx, a sinus, an ear canal, etc.

In any of the embodiments described herein the operation 11 can be repeated one or more times. For example, operation 11 can be repeated to sequentially illuminate the medium by a plurality of non-diffracting light beams, wherein each non-diffracting light beam is characterized by a different central wavelength. In embodiments in which the light beam is transmitted through the waveguide system, a sequential illumination can be achieved by sequentially filtering a polychromatic light beam, such that at each filtering the light beam is characterized by a different central wavelength. At each filtering, the light beam can be diverted along a different optical path of the same optical path prior to entering the proximal end. A representative example of these embodiments is described in the Examples section that follows (see Example 2).

The light beam can be at any wavelength range that can penetrate the medium and scatter off objects in the medium or excite molecules therein. In some embodiments of the present invention the light is at a wavelength in an infrared range (e.g., from about 700 nm to about 100 μm), in some embodiments of the present invention the light is at a near-infrared wavelength (e.g., from about 700 nm to about 1.4 μm), and in some embodiments of the present invention the light is at a visible wavelength (e.g., from about 400 nm to about 700 nm).

The method continues to 12 at which light is collected from a plurality of locations over the medium. The light can be, for example, back scattered light (e.g., when the medium does not contain fluorescent molecules, or when the light does not excite the fluorescent molecules), or it can be light emitted by the fluorescent molecules responsively to the excitation. The light is optionally and preferably collected by a pixelated imager (e.g., a CMOS or a CCD imager) so as to allow resolving the spatial distribution of the light beam received from the medium.

The method proceeds to 13 at which an image is constructed based on intensity levels of the collected light at each of the plurality of locations. This is optionally and preferably executed by an image processor that receives the intensity levels from each or at least a portion of the pixels of the imager, and generates an image in which the intensity at each location is used as a local imaging contrast.

In some embodiments of the present invention operation 11 includes illuminating the medium by two or more non-diffracting light beams, different from each other, wherein each of the beams has at least one optical characteristic (length scale, acceleration rate, waist size) that is different from the other respective characteristic(s) of the other beam(s). For example, the optical characteristics of two or more of the non-diffracting light beams can be selected such as to effect different penetration depth of the beams into the medium. These embodiments can be utilized for calculating a depth of the medium or an object in the medium, by comparison between intensity levels received for different beams. These embodiments can also be utilized for generating a plurality of images describing slices of the medium at different depths, respectively corresponding to the different beams. These embodiments can also be utilized for generating a three-dimensional (3D) image of the medium or objects in the medium, wherein the scanning and/or structured light projection provides lateral information for the 3D image, and the variation in the optical characteristics provides the depth information for the 3D image.

The method ends at 14.

Reference is now made to FIGS. 7A and 7B which are schematic illustrations of a system 80 for imaging through a medium 82, according to some embodiments of the present invention. Medium 82 is optionally and preferably a turbid medium. System 80 can comprise an illumination system 84 that illuminates medium 82 by a non-diffracting light beam 86 over a plurality of locations on a boundary 88 of medium 82. In some embodiments of the present invention illuminating system 84 sequentially illuminates medium 82 by a plurality of non-diffracting light beams, wherein each non-diffracting light beam is characterized by a different central wavelength.

Illumination system 84 typically also generates the non-diffracting light beam 86. In these embodiments, illumination system 84 can comprise a light source 100 producing a diffracting light beam 104 (typically, but not necessarily, monochromatic light beam) and a beam transforming optical element 102 that transforms beam 104 into non-diffracting beam 86. Beam transforming optical element 102 can be any element or arrangement of elements that transform the profile of a light beam to a profile of a non-diffracting beam. Representative examples including, without limitation, an annular aperture, a spatial light modulator, a holographic element, an axicon, a microaxicons, an arrangement of microaxicons, a binary phase mask, an optical fiber, an optical fiber bundle, and the like.

When optical element 102 comprises a holographic element, it can include, for example, a computer generated hologram (CGH) computationally designed, e.g., by interfering two wave fronts (e.g., a conical wave front with a plane wave). The spot size and the focal plane of the nondiffracting beam can be controlled by adjusting the width and the peak phase retardation of the wave fronts. Depending on resolution requirements, the CGH can be printed with grayscale graphics printers, with photoplotters as halftone images, or can be fabricated as chrome/iron oxide binary photomasks.

When optical element 102 comprises one or more microaxicons, the microaxicon(s) can be fabricated by multilayer lithography or etching processes.

When optical element 102 comprises an optical fiber or an optical fiber bundle, the fiber(s) can include single mode fiber(s) and multimode optical fiber(s), wherein the light beam is coupled to the single mode fiber which is coupled to the multimode fiber for generating the non-diffracting beam.

In some embodiments, optical element 102 employs a combination of techniques. For example, optical element 102 can include an optical fiber having a microaxicon, fabricated at the end of the optical fiber to control of the cone angle of the fiber. Light passing through the optical fiber passes through the microaxicon generating a non-diffracting beam.

It is expected that during the life of a patent maturing from this application many relevant techniques for transforming a light beam into a non-diffracting beam will be developed and the scope of the term Beam transforming optical element is intended to include all such new technologies a priori.

When medium 82 includes fluorescent molecules, system 84 optionally and preferably generates light beam 86 at a wavelength selected within the excitation band of the fluorescent molecules, as further detailed hereinabove.

Illumination system 84 can be a scanning system that scans medium 82 with the light beam 86. For example, illumination system 84 can be a holographic scanning system, such as, but not limited to, a holographic optical tweezers system. For example, element 102 can serve both for transforming the beam to a non-diffracting beam and for scanning the beam. Alternatively, illumination system 84 can comprise a structured light projector, such as, but not limited to, a laser combined with a micromirror array (e.g., one of the systems marketed under the trade designation TIDLP® by Texas Instruments Inc., Piano Tex., USA).

FIG. 7B is a schematic illustration of system 80 in embodiments of the invention in which illumination system 84 comprises a waveguide system 112. In these embodiments, light beam 104 from light source 100 is coupled into waveguide system 112 at its proximal end 114 and is emitted at its distal end 116. Beam transforming optical element 102 receives beam 104 at distal end 116 and transforms it into non-diffracting light beam 86. Waveguide system 112 can be, for example, an optical fiber or an optical fiber bundle. In some embodiments of the present invention system 80 comprises a beam expander and/or a collimator (not shown, see FIG. 8) at distal end 116.

In some embodiments of the present invention system 80 comprises a scanning system 118 that scans medium 82 by non-diffracting light beam 86. For example, scanning system 118 can scan the proximal end 114 of system 112 by light beam 104. These embodiments are particularly useful when waveguide system 112 comprises an optical fiber bundle, in which case the scanning can be effected by coupling beam 104 to different fibers the in fiber bundle at the proximal end 114.

In some embodiments of the present invention light beam 104 provided by light source 100 is a polychromatic light beam. In these embodiments, the system optionally and preferably comprises a sequential filter 120 that sequentially filters polychromatic light beam 104 such that at each filtering light beam 104 is characterized by a different central wavelength. Sequential filter 120 can be, for example, a filter wheel or an acusto-opto-deflector. Representative examples of these embodiments are described in the Examples section that follows (see Example 2).

System 80 can further comprise a light detecting system 90 for collecting light 106 for each location of light beam 86 over medium 82. Light detecting system 90 is preferably positioned to receive back-scattered light from medium 82. In these embodiments, light 106 is generally coaxial with, or parallel to, light 86 at boundary 88 of medium 82, except they propagate at opposite directions. This can be done, for example, using a dichroic mirror system 110 positioned in the light path of light 86 and light 106. In embodiments in which waveguide system 112 is employed, light 106 is preferably coupled into system 112 at its distal end 116, propagate along system 112 and exits at proximal end 114, from which it is diverted into light detecting system, e.g., by means of dichroic mirror system 110. In embodiments in which sequential filtering of a polychromatic light beam is employed, dichroic mirror system 110 can be configured to ensure that light beams at different central wavelengths propagate along the same optical path or alternatively to ensure that light beams at different central wavelengths propagate along different optical paths. These embodiments are illustrated in FIGS. 10A and 10B of the Examples section that follows.

When medium 82 includes fluorescent molecules, light 106 is emitted from the fluorescent molecules and it is not necessary for the detected light 106 to be coaxial with or parallel to light 86 at the boundary of medium 82.

Light detecting system 90 is optionally and preferably a camera having a CCD or CMOS imager. System 80 can further comprise an image processor 92 configured for receiving from light detecting system 90 signals 108 pertaining to intensity levels of light 106 at each of the locations, processing the intensity levels, and constructing an image based on the intensity levels, as further detailed hereinabove.

Numbered Clauses

Clause 1: A method of imaging through a medium, the method comprising:
illuminating the medium by a non-diffracting light beam over a plurality of locations on a boundary of the medium;
collecting back scattered light for each location of the non-diffracting light beam; and
constructing an image based on intensity levels of the back scattered light at each of the plurality of locations, the intensity levels constituting local contrasts over the image.

Clause 2: A method of imaging through a medium, the medium having therein fluorescent molecules, the method comprising:
illuminating the medium by a non-diffracting light beam over a plurality of locations on a boundary of the medium to excite the fluorescent molecules;
for each location of the non-diffracting light beam, collecting light emitted by the fluorescent molecules responsively to the excitation; and
constructing an image based on intensity levels of the emitted light at each of the plurality of locations, the intensity levels constituting local contrasts over the image.

Clause 3: The method according to any of clauses 1 and 2, further comprising illuminating the medium by at least one additional non-diffracting light beam, different from the non-diffracting light beam, and calculating a depth of the medium or an object in the medium based on a comparison between intensity levels received for different beams.

Clause 4: The method according to any of clauses 1-3, wherein the illuminating comprises scanning the medium by the non-diffracting light beam.

Clause 5: The method according to clause 4, wherein the scanning is by holography.

Clause 6: The method according to clause 5, wherein the scanning is by a holographic optical tweezers system.

Clause 7: The method according to any of clauses 1-3, wherein the illuminating comprises projecting a structured light beam onto the medium.

Clause 8: The method according to any of clauses 1-7, wherein the illuminating comprises sequentially illuminating the medium by a plurality of non-diffracting light beams, wherein each non-diffracting light beam is characterized by a different central wavelength.

Clause 9: The method according to any of clauses 1-3, wherein the illuminating comprises guiding a first light beam through a waveguide system having a proximal end and a distal end, and transforming the first light beam into the non-diffracting light beam at the distal end.

Clause 10: The method according to clause 9, wherein the waveguide system comprises an optical fiber.

Clause 11: The method according to clause 9, wherein the waveguide system comprises an optical fiber bundle.

Clause 12: The method according to any of clauses 9-11, wherein the waveguide system comprises a beam expander at the distal end.

Clause 13: The method according to any of clauses 9-12, wherein the waveguide system comprises a collimator at the distal end.

Clause 14: The method according to any of clauses 9-13, wherein the illuminating comprises scanning the medium by the non-diffracting light beam.

Clause 15: The method according to clause 14, wherein the waveguide system comprises an optical fiber bundle and wherein the scanning comprises scanning the proximal end by the first light beam.

Clause 16: The method according to any of clauses 9-15, wherein the medium is an internal cavity of a living body.

Clause 17: The method according to clause 16, wherein the internal cavity is a blood vessel.

Clause 18: The method according to clause 16, wherein the internal cavity is a urethra.

Clause 19: The method according to clause 16, wherein the internal cavity is a gastrointestinal tract.

Clause 20: The method according to clause 16, wherein the internal cavity is a fallopian tube.

Clause 21: The method according to clause 16, wherein the internal cavity is a pancreas.

Clause 22: The method according to clause 16, wherein the internal cavity is a bladder.

Clause 23: The method according to clause 16, wherein the internal cavity is selected from the group consisting of an esophagus, a trachea, a bronchus, a larynx, a sinus and an ear canal.

Clause 24: The method according to any of clauses 9-23, wherein the illuminating comprises sequentially illuminating the medium by a plurality of non-diffracting light beams, wherein each non-diffracting light beam is characterized by a different central wavelength.

Clause 25: The method according to clause 24, wherein the sequentially illuminating comprises sequentially filtering a polychromatic light beam, such that at each filtering the first light beam is characterized by a different central wavelength.

Clause 26: The method according to clause 25, wherein at each filtering, the first light beam is diverted along a different optical path prior to entering the proximal end.

Clause 27: The method according to clause 25, wherein at each filtering, the first light beam is diverted along the same optical path prior to entering the proximal end.

Clause 28: A system for imaging through a medium, the system comprising:

Clause an illumination system configured for illuminating the medium by a non-diffracting light beam over a plurality of locations on a boundary of the medium;

Clause a light detecting system configured for collecting light for each location of the light beam; and Clause an image processor configured for processing intensity levels of the light at each of the plurality of locations, and constructing an image based on the intensity levels, the intensity levels constituting local contrasts over the image.

Clause 29: The system according to clause 28, wherein the illumination system comprises a scanning system for scanning the medium with the light beam.

Clause 30: The system according to clause 29, wherein the scanning is by holography.

Clause 31: The system according to clause 29, wherein the scanning system comprises a holographic optical tweezers system.

Clause 32: The system according to any of clauses 28-30, wherein the illumination system comprises a structured light projector.

Clause 33: The system according to any of clauses 28-32, wherein the illuminating system is configured to sequentially illuminate the medium by a plurality of non-diffracting light beams, wherein each non-diffracting light beam is characterized by a different central wavelength.

Clause 34: The system according to any of clauses 28-30, wherein the illumination system comprises a light source configured for producing a first light beam, a waveguide system having a proximal end for receiving first light beam and a distal end for emitting the first light beam, and a beam transforming element at the distal end for transforming the first light beam into the non-diffracting light beam.

Clause 35: The system according to clause 34, wherein the waveguide system comprises an optical fiber.

Clause 36: The system according to clause 34, wherein the waveguide system comprises an optical fiber bundle.

Clause 37: The system according to any of clauses 34-36, wherein the waveguide system comprises a beam expander at the distal end.

Clause 38: The system according to any of clauses 34-37, wherein the waveguide system comprises a collimator at the distal end.

Clause 39: The system according to any of clauses 34-38, further comprising a scanning system configured for scanning the medium by the non-diffracting light beam.

Clause 40: The system according to clause 39, wherein the waveguide system comprises an optical fiber bundle and wherein the scanning system is configured for scanning the proximal end by the first light beam.

Clause 41: The system according to any of clauses 34-40, wherein the light source is configured for providing a polychromatic light beam, wherein the system comprises a sequential filter configured for sequentially filtering the polychromatic light beam such that at each filtering the first light beam is characterized by a different central wavelength.

Clause 42: The system according to clause 41, further comprising an arrangement of beam diverting elements configured to divert different central wavelengths of the first light beam along a different optical path prior to entering the proximal end.

Clause 43: The method or system according to any of clauses 1-42, wherein the non-diffracting light beam is a Bessel beam.

Clause 44: The method or system according to any of clauses 1-42, wherein the non-diffracting light beam is an Airy beam.

Clause 45: The method or system according to any of clauses 1-42, wherein the non-diffracting light beam is a super Airy beam.

Clause 46: The method or system according to any of clauses 1-42, wherein the non-diffracting light beam is a Mathieu beam.

Clause 47: The method or system according to any of clauses 1-42, wherein the non-diffracting light beam is a Weber beam.

Clause 48: The method or system according to any of clauses 1-47, wherein the non-diffracting light beam is a one-dimensional beam.

Clause 49: The method or system according to any of clauses 1-47, wherein the non-diffracting light beam is a two-dimensional beam.

Clause 50: The method or system according to any of clauses 1-49, wherein a coefficient of the non-diffracting light beam is selected to allow the non-diffracting light beam to penetrate at least 100 µm into the medium.

Clause 51: The method or system according to any of clauses 1-50, wherein the non-diffracting light beam is at an infrared wavelength.

Clause 52: The method or system according to clause 51, wherein the non-diffracting light beam is at a near-infrared wavelength.

Clause 53: The method or system according to clause 51, wherein the non-diffracting light beam is at a visible wavelength.

Clause 54: The method or system according to clause 51, wherein the image is a three-dimensional image.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Non-diffracting beams are solutions of the Helmholtz wave equation that maintain their shape over long propagation distances. Among this group of beams are the Bessel beams and the Airy beams, as well as the Mathieu and Weber beams, which are solutions to the non-paraxial Helmholtz equation. Bessel and Airy beams have been used to enhance the capabilities of Light-sheet microscopy, and Airy beams have been used to improve super-resolution stochastic optical reconstruction microscopy (STORM) [Fahrbach et al., Nature Photonics 4, 780-785 (2010); Broky et al., Optics Express 16, 12880-12891 (2008); Fahrbach et al., Nature Communications 3, 632 (2012); Vettenburg et al., Nature methods 11, 541-4 (2014); and Jia et al., Nature photonics 8, 302-306 (2014)].

Non-diffracting beams have the ability to fully reconstruct after encountering a partial obstacle. The present Example uses such beams to increase the penetration depth of laser scanning microscopy. Objects immersed in highly scattering media are imaged by scanning a non-diffracting laser beam.

A schematic illustration of the experimental system used in the present Example is shown in FIG. 1. The laser beam is scanned horizontally and propagates perpendicularly to the imaged plane, in a similar configuration used for confocal microscopy. Upon encountering an object the beam is reflected, illuminating the sample with scattered light. The total intensity of the resulting back scattered light at each beam position is used as the imaging contrast. Alternatively, the scanning beam can be used to excite fluorescent markers to achieve composition sensitive contrast.

Referring to FIG. 1, the experimental setup included a dual objective microscope based on an Olympus upright/inverted X71 Olympus microscope. A spinning disk confocal microscope (Andor, Revolution XD) was mounted on the top (upright) part, while a holographic optical tweezers (HOTs) setup was incorporated through the bottom (inverted) part.

The confocal imaging system was equipped with a Yokogawa (CSU-X1) spinning disc and an Andor (iXon 897) EM-CCD camera. To acquire three-dimensional images, the objective lens (Olympus UPlanFLN, ×60, NA=1.25, oil immersion) was mounted on a piezoelectric scanner (Physik Instrumente, Pifoc P-721.LLQ) and consecutive slices of the sample were recorded with 100 nm axial resolution.

The HOTs was based on an Ytterbium doped fiber laser (Keopsys, KPS-KILAS-TRAPP-1083-20-PM-CO) with an emission wavelength of 1083 nm and maximal power output of 20 W. Beam shaping and scanning was performed using a computer controlled liquid crystal spatial light modulator (SLM, Hamamatsu X10468-07). A HOTs setup operating with a DPSS laser (Coherent, Verdi 6 W) at a wavelength of 532 nm was also used, as an alternative.

The HOTs setup was used to create and scan the non-diffracting laser beams, and the confocal module was used to image the beams in clear and turbid media.

Figure 2A:
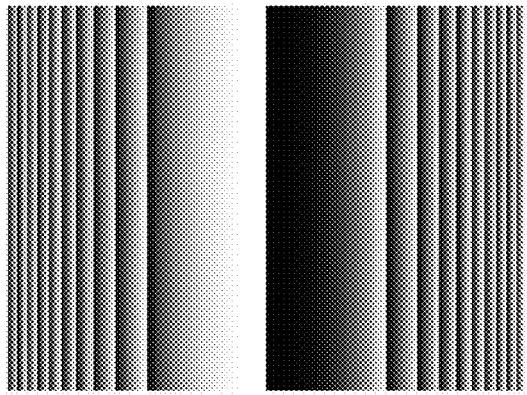
Figure 2B:
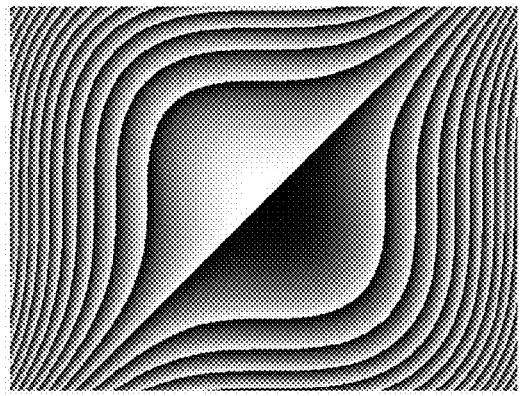
Figure 2C:
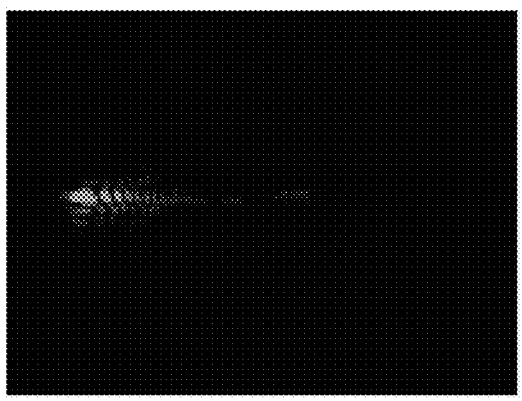
Figure 2D:
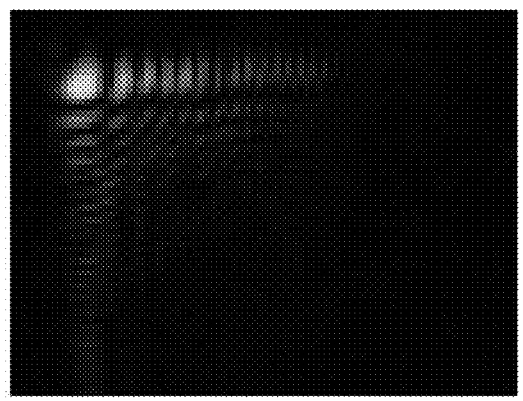
Figure 2E:
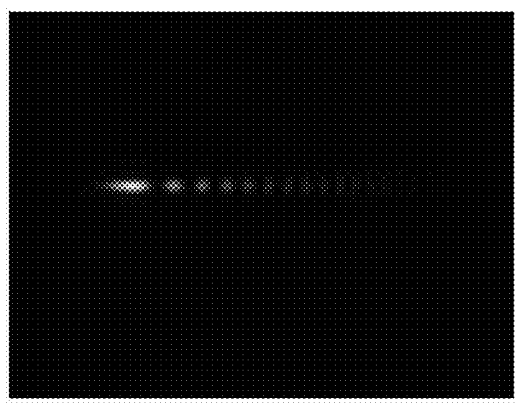
Figure 2F:
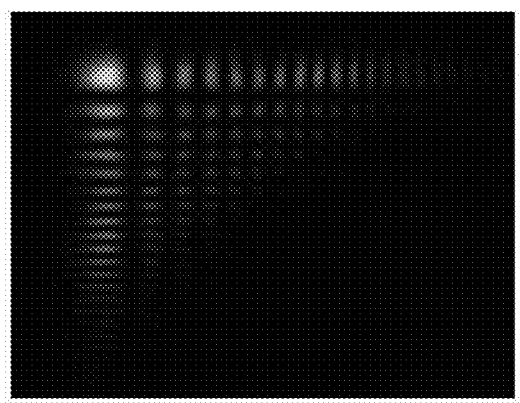

FIGS. 2A and 2B shows phase masks of 1D and 2D Airy beam that were imposed by the SLM. The reflections of the resulted 1D and 2D Airy beams are shown in FIGS. 2C and 2D and the corresponding simulation results are shown in FIGS. 2E and 2F. Each of these beams had a scaling parameter (see below) of 60.

An accelerating beam, such as Airy, Weber, and Mathieu beams, can be used to gage the depth of the imaged object. In the present Example, several characteristics of the accelerating non-diffracting beams are investigated. The length scale over which the beam maintains it original shape is selected to be sufficiently large, so as to allow imaging at sufficient depth. The beam waist is selected sufficiently narrow so as to allow imaging at sufficient lateral resolution. The acceleration rate of the beam reduces the penetration depth, but increases the beam's average intensity. Another property that is investigated in the present Example is the ability to self-reconstruct in turbid media which is advantageous for imaging and which further improves the penetration depth.

Figure 3:
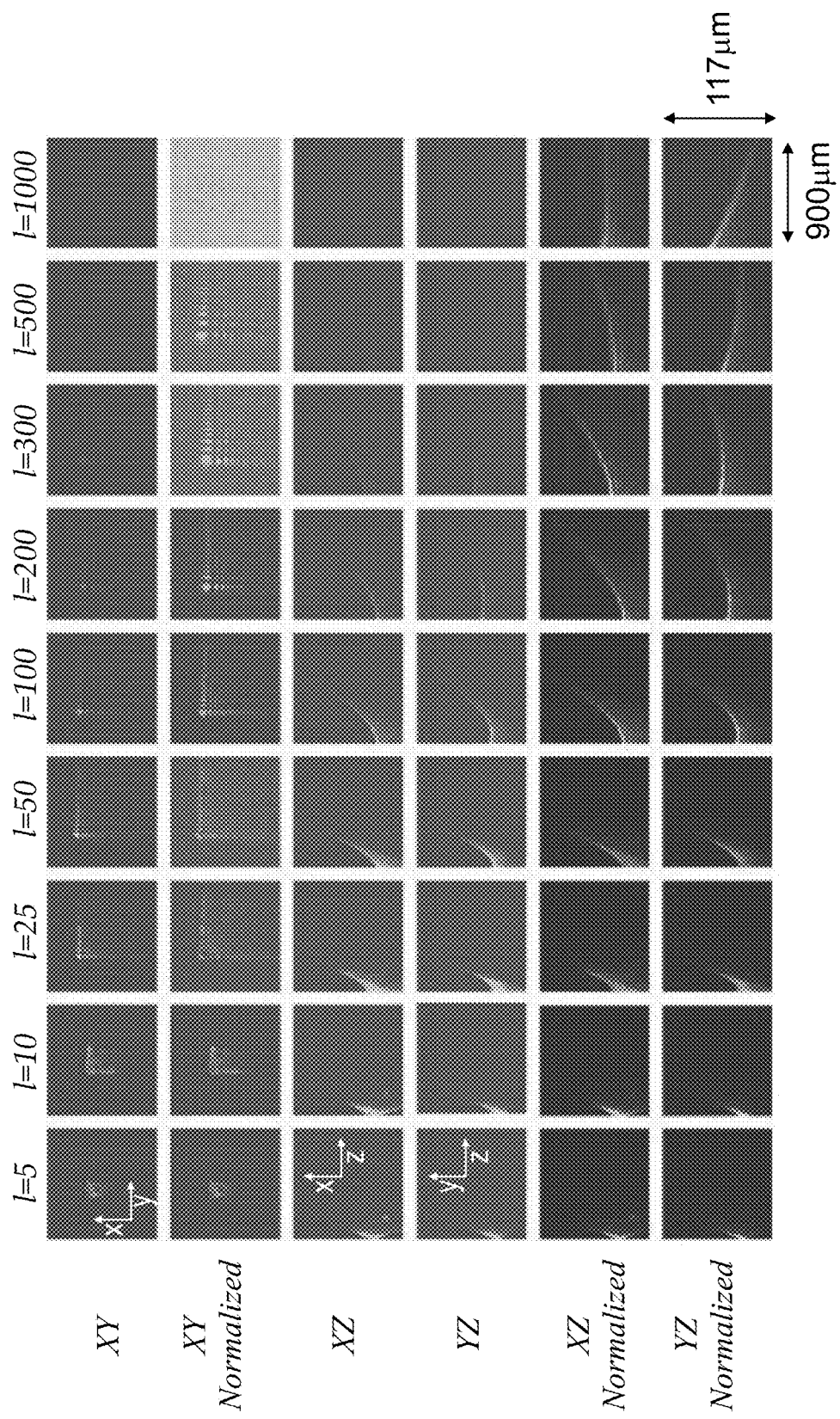

Airy beams in clear media are characterized by their scaling parameters. Airy beams are created using the following phase profile, $\phi = \vec{x}^3 2\pi \ell$, where $\vec{x}$ is normalized by the number of pixels in the SLM and $\ell$ is a scaling parameter. FIG. 3 shows microscope images of Airy beams reflected from a mirror with different values of the scaling parameter $\ell$. Shown are 2D projections of the Airy beams on the XY and XZ planes with and without normalization. The projections were created from 3D beam structure obtain by collecting sections in growing axial distance from the focal plane. As shown, the penetration depth decreases as the acceleration increases, and the total intensity of the beams decreases with decreasing acceleration. A representative compromise between acceleration rate, penetration depth and brightness was found with $\ell=100$, but other values for $\ell$ are also contemplated.

Figure 4A:
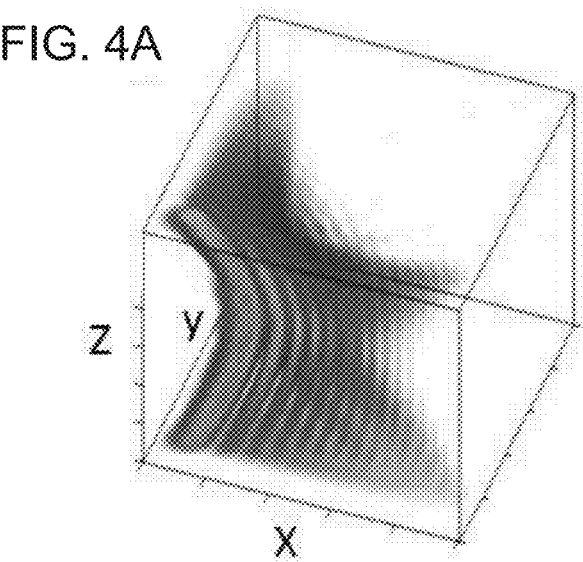
Figure 4B:
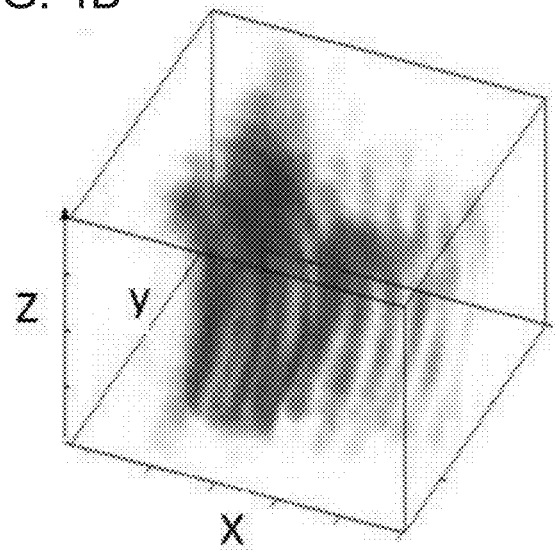
Figure 4C:
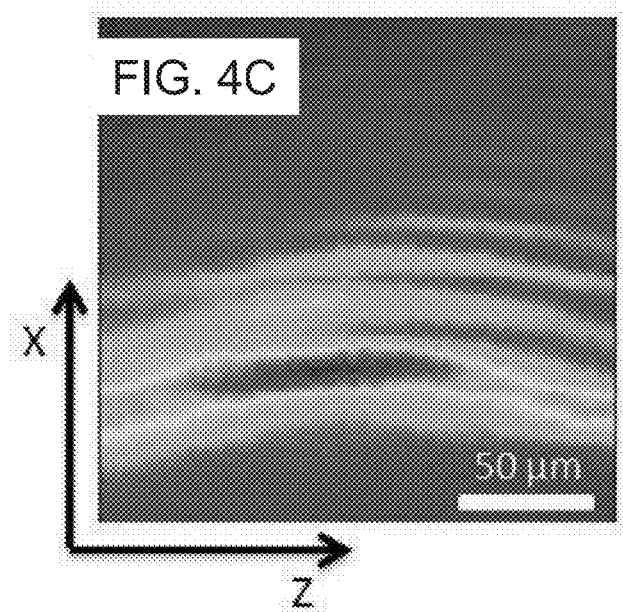
Figure 4D:
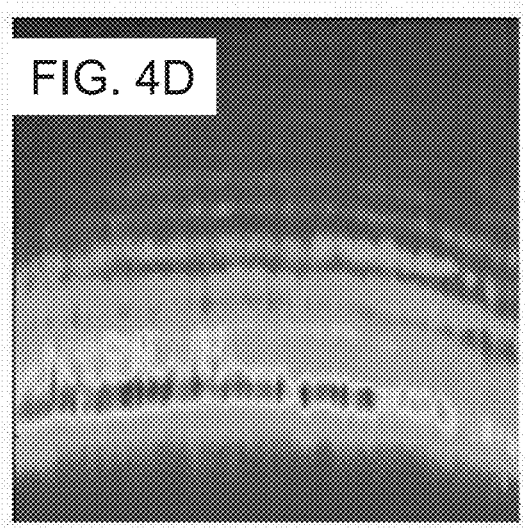

To characterize the self-reconstruction properties of the Airy beams an $\ell=100$ Airy beam was projected through water and through 200 μm of milk (3% fat, Tnuva, Israel). In both cases, the beam was imaged directly using the spinning disk confocal. The 3D structure of the beam in water as compared to the calculated shape is presented in FIGS. 4A and 4B. FIGS. 4C and 4D show the intensity distribution and shape of the beams in double distilled water (FIG. 4C) and milk (FIG. 4D) as projected on the XZ plane. As shown, the beam shape does not change along the beam's propagation path, but the intensity distribution along it does. In the turbid medium (milk, in the present Example) the beam's intensity is brightest near the focal plane (z=0) and then decays along the beam's propagation path.

In the clear medium (water, in the present Example), the beam is brightest at the highest acceleration region (where the beam's curvature is maximal). It was found by the present Inventors that a sufficient portion of the beam's energy survives while the beam propagates in the turbid medium even at a penetration depth of 200 μm. This allows internal imaging, as demonstrated below.

Milk/water mixtures in different concentrations were used as the model turbid media, and a gold pattern evaporated on the far wall of the sample was imaged. FIGS. 5A-K show the results of the imaging experiments. FIG. 5A shows a transmission optical microscopy image of the sample, a two scale gold pattern on glass, in the present Example; FIGS. 5B and 5C show a line scan perpendicular to the gold pattern using an Airy beam (FIG. 5B) and using a Gaussian beam (FIG. 5C) at various milk concentrations (20-40% milk); FIGS. 5D-5G show reconstructed images of the sample at 0%, 20%, 30% and 40% milk, respectively with an $\ell=100$ Airy beam; and FIGS. 5H-5K show reconstructed images of the sample at 0%, 20%, 30% and 40% milk, respectively, with a Gaussian beam.

Initially, an Airy beam was scanned over the gold pattern immersed in water, measuring the reflection from the sample at a region surrounding the reflection of the main Airy lobe. This measurement was used to reconstruct an image, which was then compared to conventional bright-field microscopy (see FIGS. 5A and 5D) and to the same imaging protocol using a Gaussian beam instead of an Airy beam. This experiment was repeated for a sample immersed in a milk/water mixture (see FIGS. 5E-G), using laser light at wavelength λ=532 nm. This wavelength was selected since its absorption coefficient in milk is higher than in NIR.

The imaged gold pattern was in the form of a rectangle, 50 μm in width, and a line, 2 μm in width. When immersed in water, the two-scaled pattern was successfully reconstructed using both Airy and Gaussian beams. Comparing both beam types at gradually increasing milk concentrations demonstrates the advantage of the Airy beam. For milk concentrations of up to 50% the narrow line is observed with the Airy beam (FIGS. 5E and 5F), but not with the Gaussian beam (FIGS. 5I and 5J). This is also shown in FIGS. 5B and 5C where the intensity of the reconstructed image along a line perpendicular to the narrow gold stripe is plotted for a sample within water (insets) and different milk concentrations (20-40%). The experiments demonstrate that a Gaussian beam (FIG. 5C) cannot discern the gold line when immersed in the turbid medium, as opposed to scans with an Airy beam (FIG. 5B). For the larger features (the 50 μm rectangle, in the present Example) the advantage of the Airy beam is observed at higher milk concentrations, e.g., 40% (compare FIGS. 5G and 5H).

This Example demonstrates a technique for label free imaging through turbid media based on reflection contrast. The imaging quality depends on the absorption coefficient of the scanning laser light. This can be tailored to the sample by an appropriate selection of the illuminating wavelength, for example, in milk and other biological samples absorption is minimized using near infrared radiation.

The resolution of the imaging technique of the present embodiments depends on the width of the scanning non-diffracting beam. By modifying the beam mode, for example, using super Airy beams, the resolution can be improved. The imaging technique of the present embodiments can also be applied for three-dimensional imaging using the shift in axial position of the reflected beam as a function of the depth from which it is reflected. In addition, scanning a sample with several Airy beams with different acceleration and penetration depths can be used to measure the depth of a sample. The imaging technique of the present embodiments can also be used with fluorescence as a contrast agent instead of reflection, where the Airy beam is used to excite fluorescence at a given position and the total of the returning light is collected.

The imaging technique of the present embodiments can be useful for microscopic as well as macroscopic objects, since the penetration depth increases significantly, reaching several millimeters when the resolution requirements are relaxed.

Example 2

The present Example describes embodiments suitable for providing a view through body fluids for medical applications. While the embodiments below are described with a particular emphasis to imaging within blood vessels, it is to be understood that other medical applications, including, without limitation, imaging within the urethra, the gastrointestinal tract, the esophagus, the trachea, the bronchus, the fallopian tube, the pancreas, the larynx, the sinus, the ear canal, and the bladder.

In the present Example, a portable version of the imaging system of Example 1 is employed. The portable version optionally and preferably includes optical elements suitable for being introduced into the human body. In various exemplary embodiments of the invention a light beam is generated outside the imaged cavity. The light beam is then carried by means of a waveguide system, such as, but not limited to, an optical fiber or an optical fiber bundle to the cavity. It is recognized by the Inventor that the optical fiber does not retain the beam characteristics such as its phase. Thus, the non-diffracting property of the beam is preferably imparted to the light beam after the beam had propagated through the fiber. This can be done, for example, by placing the beam transforming optical element at the distal end of the waveguide system.

FIG. 8 is a schematic illustration of a system for imaging through a medium, according to embodiments of the present invention in which a non-diffracting light beam is formed at the distal end of a waveguide system. A light source (a laser, in the illustration of FIG. 8) is coupled, typically by an optical coupler (a fiber coupler, in the illustration of FIG. 8)

to a waveguide system (an optical fiber, in the illustration of FIG. 8). The beam propagates within the waveguide system. The non-diffracting property of the beam is imparted to the beam by a beam transforming optical element (a phase plate, in the illustration of FIG. 8) mounted on the distal end of the waveguide system. For example, the beam transforming optical element can transform the beam into an Airy beam. Mounting the beam transforming optical element at the distal end of the fiber ensures that the shaped beam does not lose its properties inside the optical fiber, where it may be altered due to the fiber coiling and manipulations during the procedure. The non-diffracting light beam propagates in the body fluid (e.g., blood, urine, etc) until it encounters a reflecting surface, and is reflected thereby. The back-reflected light can then enter the fiber, through the beam transforming optical element, and propagate in the opposite direction to a detector.

In some embodiments of the present invention, the light beam from the light source passes through a half waveplate and/or a polarizing beam splitter and is then coupled to the waveguide system. The advantage of these embodiments is that the signal to noise ratio is enhanced. In these embodiments, only the depolarized returning light beam, which propagated through the turbid fluid reaches the detector.

In some embodiments of the present invention a beam expander (e.g., an achromatic beam expander) and a collimator are mounted at the distal end of the waveguide system, between the waveguide system and the beam transforming optical element.

The beam transforming optical element can be embodied as any device suitable for being mounted on a waveguide system and capable of transforming the light beam exiting the waveguide system into a non-diffracting light beam. Representative examples including, without limitation, one or more micro-lens [e.g., a polymeric micro-lens such as, but not limited to, the polymeric micro-lens disclosed in Ribeiro, et al., OFS2014 23rd Int. Conf. Opt. Fiber Sensors 9157, 91573K-91573K-4 (2014)], a photonic structure (e.g., a photonic structure imprinted by Femtosecond Laser Multiphoton Polymerization (FLMP) on silica based sol-gel as disclosed in Malinauskas et al., in Proceedings of SPIE—The International Society for Optical Engineering, H. Thienpont, P. Van Daele, J. Mohr, and H. Zappe, eds. (2010), Vol. 7716, p. 77160A-77160A-12; and Malinauskas et al., J. Opt. 12, 035204/1-8 (2010)], a resin phase plate [e.g., a resin phase plate fabricated by nanoimprint lithography, as disclosed Calafiore et al., Nanotechnology 27, 375301 (2016)].

In some embodiments of the present invention a polychromatic light beam or a plurality of monochromatic light beams are employed.

FIG. 9 shows relative intensity reflected from a target as measured using the experimental system described in Example 1, using a laser working at a wavelength of 532 nm. As shown, the reflection depends on color. Compare, for example, the reflection from red and yellow surfaces.

A polychromatic light beam or a plurality of monochromatic light beams can be generated, for example, by a multi-colored coherent light source. A representative example includes, without limitation, a commercially available supercontinuum laser. Preferably, a filter-wheel or an acusto-opto-deflector (AOD) is positioned after the light source, optionally and preferably immediately after the light source, to allow active switching between the different spectral bands. Each spectral band can be characterized, for example, by a central wavelength and a spectral width.

In some embodiments of the present invention, the spectral band of the half waveplate and the polarizing beam splitter is selected to cover the range of wavelengths to be transmitted through the waveguide system. Alternatively, each spectral band can be deflected to a different optical path. In these embodiments a set of dichroic mirrors can be used to selectively redirect the respective spectral band to along the respective optical path.

FIGS. 10A and 10B are schematic illustrations, showing two techniques suitable for coupling a polychromatic light beam into a waveguide system according to some embodiments of the present invention. The polychromatic light beam can be produced a supercontinuum laser, and be filtered by a filter wheel or an AOD to remove undesired spectral components allowing only one spectral band to continue. The filtering can be sequential so that different spectral bands continue at different times. In FIG. 10A, a broadband half wave plate $\lambda/2$ and a polarizing beam splitter PBS are used for all the spectral bands. In FIG. 10B, different light paths are used for different spectral bands. Shown in FIG. 10B is a set of dichroic mirrors DM and regular mirrors M that create the different optical paths. The advantage of this configuration is that it allows a larger variability in the wavelength.

A beam expander and collimator (not shown, see FIG. 8) can be mounted at the distal end of the waveguide system. The response of the same phase plate to different spectral bands is manifested in a rescaling of the resulting beam shape, and in a change in efficiency, but not in a distortion of the beam. Therefore, by considering the rescaling of the beam shape, the same phase plate can be used for different spectral bands.

Beam scanning can be done manually or automatically. In some embodiments of the present invention scanning is effected by moving the waveguide system. Alternatively or additionally scanning can be effected by a fiber bundle, wherein the beam is stirred into one of the fibers that form the bundle, as schematically illustrated in FIGS. 11A-C. FIG. 11A illustrates a cross-sectional view of a fiber bundle having a plurality of optical fibers enclosed in a cladding layer. FIG. 11B illustrates a cross-sectional view at the distal end of the fiber bundle, wherein an array of phase masks is mounted, optionally and preferably after the beam expander and the collimator (not shown, see FIG. 11C). The phase masks encode the non-diffracting beam shape and optionally and preferably also aberration corrections. Preferably, a separate phase mask is placed to receive light beam from each fiber in the bundle. FIG. 11C illustrates a side view of the system, showing the laser source providing a light beam, and a beam steering system scanning the light beam across the proximal end of the optical fiber bundle, wherein different optical fibers receive the beam at different times. The steering system can be, for example, galvo-mirror or an AOD.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] D. Psaltis and I. N. Papadopoulos, "Imaging: The fog clears," Nature 491, 197-198 (2012).
[2] O. Katz, E. Small, Y. Guan, and Y. Silberberg, "Noninvasive nonlinear focusing and imaging through strongly scattering turbid layers," Optica 1, 170 (2014).
[3] O. Katz, E. Small, and Y. Silberberg, "Looking around corners and through thin turbid layers in real time with scattered incoherent light," Nat. Photonics 6, 549-553 (2012).
[4] A. P. Mosk, A. Lagendijk, G. Lerosey, and M. Fink, "Controlling waves in space and time for imaging and focusing in complex media," Nat. Photonics 6, 283-292 (2012).
[5] V. V Tuchin, "Optical clearing of tissues and blood using the immersion method," J. Phys. D. Appl. Phys. 38, 2497-2518 (2005).
[6] M. R. Hee, E. A. Swanson, J. A. Izatt, J. M. Jacobson, and J. G. Fujimoto, "Femtosecond transillumination optical coherence tomography," Opt. Lett. 18, 950 (1993).
[7] C. Dunsby and P. M. W. French, "Techniques for depth-resolved imaging through turbid media including coherence-gated imaging," J. Phys. D. Appl. Phys. 36, R207-R227 (2003).
[8] V. Ntziachristos, "Going deeper than microscopy: the optical imaging frontier in biology," Nat. Methods 7, 603-614 (2010).
[9] Y. Roichman, D. Kasimov, E. Dekel, "Method and system for imaging turbid media," (2016).
[10] L. J. Shaw, T. H. Marwick, W. A. Zoghbi, W. G. Hundley, C. M. Kramer, S. Achenbach, V. Dilsizian, M. J. Kern, Y. Chandrashekhar, and J. Narula, "Why all the focus on cardiac imaging?," JACC Cardiovasc. Imaging 3, 789-794 (2010).
[11] N. Bosschaart, G. J. Edelman, M. C. G. Aalders, T. G. Van Leeuwen, and D. J. Faber, "A literature review and novel theoretical approach on the optical properties of whole blood," Lasers Med. Sci. 29, 453-479 (2014).
[12] Y. Uchida, "Advances in Angioscopic Imaging of Vascular Disease," World J. Cardiovasc. Surg. 2, 114-131 (2012).
[13] R. Puri, M. I. Worthley, and S. J. Nicholls, "Intravascular imaging of vulnerable coronary plaque: current and future concepts," Nat. Rev. Cardiol. 8, 131-139 (2011).
[14] D. Vancraeynest, A. Pasquet, V. Roelants, B. L. Gerber, and J.-L. J. Vanoverschelde, "Imaging the vulnerable plaque," J. Am. Coll. Cardiol. 57, 1961-1979 (2011).
[15] N. Guo, A. Maehara, G. S. Mintz, Y. He, K. Xu, X. Wu, A. J. Lansky, B. Witzenbichler, G. Guagliumi, B. Brodie, M. A. Kellett, O. Dressler, H. Parise, R. Mehran, and G. W. Stone, "Incidence, Mechanisms, Predictors, and Clinical Impact of Acute and Late Stent Malapposition After Primary Intervention in Patients With Acute Myocardial Infarction," Circulation 122, (2010).
[16] B. D. MacNeill, H. C. Lowe, M. Takano, V. Fuster, and I.-K. Jang, "Intravascular Modalities for Detection of Vulnerable Plaque," Arterioscler. Thromb. Vasc. Biol. 23, (2003).
[17] Y. Uchida, "Recent advances in coronary angioscopy," J. Cardiol. 57, 18-30 (2011).
[18] Y. Honda and P. J. Fitzgerald, "Stent Thrombosis," Circulation 108, (2003).
[19] R. S. R. Ribeiro, R. B. Queirós, A. Guerreiro, C. Ecoffet, O. Soppera, and P. A. S. Jorge, "Fiber optical beam shaping using polymeric structures," OFS2014 23rd Int. Conf. Opt. Fiber Sensors 9157, 91573K-91573K-4 (2014).
[20] M. Malinauskas, H. Gilbergs, A. Zukauskas, K. Belazaras, V. Purlys, M. Rutkauskas, G. Bickauskaite, A. Momot, D. Paipulas, R. Gadonas, S. Juodkazis, and A. Piskarskas, "Femtosecond laser fabrication of hybrid micro-optical elements and their integration on the fiber tip," in Proceedings of SPIE—The International Society for Optical Engineering, H. Thienpont, P. Van Daele, J. Mohr, and H. Zappe, eds. (2010), Vol. 7716, p. 77160A-77160A-12.
[21] M. Malinauskas, H. Gilbergs, A. ukauskas, V. Purlys, D. Paipulas, and R. Gadonas, "A femtosecond laser-induced two-photon photopolymerization technique for structuring microlenses," J. Opt. 12, 035204/1-8 (2010).
[22] G. Calafiore, A. Koshelev, F. I. Allen, S. Dhuey, S. Sassolini, E. Wong, P. Lum, K. Munechika, and S. Cabrini, "Nanoimprint of a 3D structure on an optical fiber for light wavefront manipulation," Nanotechnology 27, 375301 (2016).
[23] S.-H. Lee and D. G. Grier, "Robustness of holographic optical traps against phase scaling errors," 13, 7458-7465 (2005).

What is claimed is:

1. A method of imaging through a medium, the method comprising:
   illuminating the medium by a non-diffracting light beam over a plurality of locations on a boundary of the medium;
   collecting back scattered light for each location of said non-diffracting light beam; and
   constructing an image based on intensity levels of said back scattered light at each of said plurality of locations, said intensity levels constituting local contrasts over said image;
   wherein said illuminating comprises sequentially illuminating the medium by a plurality of non-diffracting light beams, wherein each non-diffracting light beam is characterized by a different central wavelength.

2. The method according to claim 1, further comprising illuminating the medium by at least one additional non-diffracting light beam, different from said non-diffracting light beam, and calculating a depth of the medium or an object in the medium based on a comparison between intensity levels received for different beams.

3. The method according to claim 1, wherein said illuminating comprises scanning the medium by said non-diffracting light beam.

4. The method according to claim 3, wherein said scanning is by holography.

5. The method according to claim 4, wherein said scanning is by a holographic optical tweezers system.

6. The method according to claim 1, wherein said illuminating comprises projecting a structured light beam onto the medium.

7. The method according to claim 1, wherein said illuminating comprises guiding a first light beam through a waveguide system having a proximal end and a distal end, and transforming said first light beam into said non-diffracting light beam at said distal end.

8. The method according to claim 7, wherein said waveguide system comprises an optical fiber.

9. The method according to claim 7, wherein said medium is an internal cavity of a living body.

10. The method according to claim 7, wherein said sequentially illuminating comprises sequentially filtering a polychromatic light beam, such that at each filtering said first light beam is characterized by a different central wavelength.

11. The method according to claim 1, wherein said non-diffracting light beam is selected from the group consisting of a Bessel beam, an Airy beam, a super Airy beam, a Mathieu beam, and a Weber beam.

12. The method according to claim 1, wherein said non-diffracting light beam is a one-dimensional beam.

13. The method according to claim 1, wherein said non-diffracting light beam is a two-dimensional beam.

14. The method according to claim 1, wherein said non-diffracting light beam is at an infrared wavelength.

15. The method according to claim 14, wherein said image is a three-dimensional image.

16. A method of imaging through a medium, the medium having therein fluorescent molecules, the method comprising:
- illuminating the medium by a non-diffracting light beam over a plurality of locations on a boundary of the medium to excite the fluorescent molecules;
- for each location of said non-diffracting light beam, collecting light emitted backwardly by the fluorescent molecules responsively to said excitation; and
- constructing an image based on intensity levels of said emitted light at each of said plurality of locations, said intensity levels constituting local contrasts over said image;
- wherein said illuminating comprises sequentially illuminating the medium by a plurality of non-diffracting light beams, wherein each non-diffracting light beam is characterized by a different central wavelength.

17. A system for imaging through a medium, the system comprising:
- an illumination system configured for illuminating the medium by a non-diffracting light beam over a plurality of locations on a boundary of the medium;
- a light detecting system configured for collecting light emitted or scattered backwardly for each location of said light beam; and
- an image processor configured for processing intensity levels of said light at each of said plurality of locations, and constructing an image based on said intensity levels, said intensity levels constituting local contrasts over said image;
- wherein said illuminating system is configured to sequentially illuminate the medium by a plurality of non-diffracting light beams, wherein each non-diffracting light beam is characterized by a different central wavelength.

18. The system according to claim 17, wherein said illumination system comprises a scanning system for scanning the medium with said light beam.

19. The system according to claim 18, wherein said scanning is by holography.

20. The system according to claim 18, wherein said scanning system comprises a holographic optical tweezers system.

21. The system according to claim 17, wherein said illumination system comprises a structured light projector.

22. The system according to claim 17, wherein said illumination system comprises a light source configured for producing a first light beam, a waveguide system having a proximal end for receiving first light beam and a distal end for emitting said first light beam, and a beam transforming element at said distal end for transforming said first light beam into said non-diffracting light beam.

* * * * *